(12) United States Patent
Ward et al.

(10) Patent No.: US 12,053,425 B2
(45) Date of Patent: *Aug. 6, 2024

(54) HIGH-RESOLUTION, SELECTIVE AND SELF-OPTIMIZING HAPTIC AND ELECTROTACTILE DISPLAY AND METHODS OF USE

(71) Applicant: Purdue Research Foundation, West Lafayette, IN (US)

(72) Inventors: Matthew P. Ward, Indianapolis, IN (US); Pedro P. Irazoqui, West Lafayette, IN (US); Muhammad Abdullah Arafat, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 989 days.

This patent is subject to a terminal disclaimer.

(21) Appl. No.: 16/732,064

(22) Filed: Dec. 31, 2019

(65) Prior Publication Data

US 2020/0345578 A1 Nov. 5, 2020

Related U.S. Application Data

(63) Continuation of application No. 15/167,527, filed on May 27, 2016, now Pat. No. 10,517,791.

(Continued)

(51) Int. Cl.
*A61H 23/00* (2006.01)
*A61B 5/00* (2006.01)
(Continued)

(52) U.S. Cl.
CPC ............... *A61H 23/02* (2013.01); *A61B 5/24* (2021.01); *A61B 5/4836* (2013.01);
(Continued)

(58) Field of Classification Search
CPC ................ A61H 23/02; A61H 23/0218; A61H 2201/0207; A61H 2201/0214;
(Continued)

(56) References Cited

U.S. PATENT DOCUMENTS 6,231,531 B1 5/2001 Lum et al.
10,517,791 B2 * 12/2019 Ward ....................... H04L 67/00
(Continued)

*Primary Examiner* — Timothy A Stanis
(74) *Attorney, Agent, or Firm* — Reichel Stohry Dean LLP; Natalie J. Dean; Mark C. Reichel

(57) ABSTRACT

High-resolution, selective, and self-optimizing haptic and electrotactile display and methods of use. In an embodiment of a feedback system referenced herein, the feedback system includes a prosthesis configured to be worn by an individual, including at least one prosthesis sensor configured to detect a state or condition in an environment of the at least one prosthesis sensor, and at least one actuator in communication with the at least one prosthesis sensor and configured to receive data relating to the detected state or condition and to stimulate a nerve of the individual; a neural sensor positioned upon or within the individual, configured to detect a neural response relating to the stimulation of the nerve by the at least one actuator; and a processor in communication with at least one of the at least one prosthesis sensor, at least one of the at least one actuator, and the neural sensor.

20 Claims, 30 Drawing Sheets

Related U.S. Application Data

(60) Provisional application No. 62/167,141, filed on May 27, 2015.

(51) Int. Cl.
| | | |
|---|---|---|
| *A61B 5/24* | (2021.01) | |
| *A61F 2/50* | (2006.01) | |
| *A61H 23/02* | (2006.01) | |
| *A61N 1/04* | (2006.01) | |
| *A61N 1/05* | (2006.01) | |
| *H04L 67/00* | (2022.01) | |
| *H04L 67/12* | (2022.01) | |
| *A61F 2/48* | (2006.01) | |
| *A61N 1/00* | (2006.01) | |

(52) U.S. Cl.
CPC .......... *A61B 5/4851* (2013.01); *A61B 5/6811* (2013.01); *A61B 5/7455* (2013.01); *A61H 23/0218* (2013.01); *A61N 1/0456* (2013.01); *A61N 1/0551* (2013.01); *H04L 67/00* (2013.01); *H04L 67/12* (2013.01); *A61F 2/482* (2021.08); *A61F 2/50* (2013.01); *A61H 2201/0207* (2013.01); *A61H 2201/0214* (2013.01); *A61H 2201/0285* (2013.01); *A61H 2201/10* (2013.01); *A61H 2201/5002* (2013.01); *A61H 2201/5007* (2013.01); *A61H 2201/5012* (2013.01); *A61H 2201/5043* (2013.01); *A61H 2201/5071* (2013.01); *A61H 2201/5082* (2013.01); *A61H 2205/027* (2013.01); *A61H 2230/105* (2013.01); *A61N 1/00* (2013.01)

(58) Field of Classification Search
CPC ........ A61H 2201/0285; A61H 2201/10; A61H 2201/5002; A61H 2201/5007; A61H 2201/5012; A61H 2201/5043; A61H 2201/5071; A61H 2201/5082; A61H 2205/027; A61H 2230/105; A61B 5/24; A61B 5/4836; A61B 5/4851; A61B 5/6811; A61B 5/7455; A61B 5/389; A61N 1/0456; A61N 1/0551; A61N 1/00; H04L 67/00; H04L 67/12; A61F 2/482
See application file for complete search history.

(56) References Cited

U.S. PATENT DOCUMENTS

| | | |
|---|---|---|
| 2009/0048539 A1 | 2/2009 | Lundborg |
| 2014/0031952 A1 | 1/2014 | Harshbarger et al. |
| 2014/0207252 A1* | 7/2014 | Karr ................... A61N 1/3605 623/25 |
| 2014/0236176 A1 | 8/2014 | Jung et al. |
| 2014/0277739 A1 | 9/2014 | Kornbluh et al. |
| 2016/0143751 A1* | 5/2016 | Chestek ................ A61F 2/72 623/25 |
| 2016/0248361 A1* | 8/2016 | Elenga ................ H02K 33/16 |

* cited by examiner

FIG. 8

| Classification | Diameter (μm) | Conduction Velocity (m/s) | Function(s) |
|---|---|---|---|
| Aα | 13-22 | 70-120 | • Motor: Alpha motoneurons<br>• Sensory: Touch, muscle spindle primary endings, Golgi tendon organs |
| Aβ | 8-13 | 40-70 | • Motor: Beta motoneurons<br>• Sensory: Touch, kinesthesia, muscle spindle secondary endings |
| Aγ | 4-8 | 15-40 | • Motor: Gamma motoneurons<br>• Sensory: Touch, pressure |
| Aδ | 1-4 | 5-15 | • Sensory: Pain, crude touch, pressure, temperature |
| B | 1-3 | 3-14 | • Autonomic: Preganglionic |
| C | 0.1-1 | 0.2-2 | • Sensory: Pain, touch, pressure, temperature<br>• Autonomic: Postganglionic |

FIG. 10C  *Letter System*

| Classification | Diameter (μm) | Conduction Velocity (m/s) | Function(s) |
|---|---|---|---|
| Ia | 12-20 | 70-120 | • Sensory: Muscle spindle primary endings |
| Ib | 11-19 | 66-114 | • Sensory: Golgi tendon organs |
| II | 5-12 | 20-50 | • Sensory: Touch, muscle spindle primary endings, kinesthesia |
| III | 1-5 | 4-20 | • Sensory: Pain, crude touch, pressure, temperature |
| IV | 0.1-2 | 0.2-3 | • Sensory: Pain, touch, pressure, temperature |

FIG. 10D  *Roman Numeral System*

HIGH-RESOLUTION, SELECTIVE AND SELF-OPTIMIZING HAPTIC AND ELECTROTACTILE DISPLAY AND METHODS OF USE

PRIORITY

The present application is related to, claims the priority benefit of, and is a U.S. continuation patent application of U.S. patent application Ser. No. 15/167,527 to Ward et al., filed May 27, 2016, which: (a) issues as U.S. Pat. No. 10,517,791 on Dec. 31, 2019, and (b) is related to, and claims the priority benefit of, U.S. Provisional Patent Application Ser. No. 62/167,141, filed May 27, 2015. The contents of each of the foregoing applications and patent are hereby incorporated by reference in their entireties into this disclosure. The present application also incorporates by reference the entirety of U.S. Provisional Patent Application Ser. No. 61/550,584, filed Oct. 24, 2011, the entirety of International Patent Application Serial No. PCT/US2012/061687, filed Oct. 24, 2012, and the entirety of U.S. patent application Ser. No. 14/349,511, filed Apr. 3, 2014.

BACKGROUND

Regarding the electrode-tissue interface, selective activation or inhibition of a specific fiber group is an ongoing challenge. Strategies include altering the shape or pattern of the electrical stimulus, using a multi-channel cuff electrode, and using a more invasive microelectrode array. Many investigators have demonstrated enhanced control of target neuron populations using microelectrode arrays that penetrate the nerve with needle-like probes (e.g., the Utah Array) or flatten the nerve onto an array of planar electrodes (e.g., the Flat Interface Nerve Electrode, or FINE). Since the recording/stimulating sites can be placed nearer the target neurons, selectivity and control is improved. The advantage of these alternative electrode configurations comes at the expense of invasiveness and increased risk of nerve damage. Furthermore, the success of these alternative electrode configurations is largely dictated by a priori knowledge of target fiber location(s) in the nerve, significant experience and perhaps a bit of luck. While an optimal solution is a noninvasive therapy, a therapy employing some variant of the cuff electrode is the next best thing.

While a cuff electrode is generally safer and less invasive than microelectrode arrays that penetrate or flatten the nerve, their current designs are not ideal for selective nerve stimulation or control. Cuff electrodes make circumferential electrical contact with a nerve trunk or branch. With this configuration, all axons in the nerve are exposed to the excitatory and/or inhibitory stimuli, more so at the periphery due to a closer proximity to the source of the energy. Since all axons are exposed to the stimulus, it logically follows that all neurons may be activated if a strong enough stimulus is provided (in terms of pulse duration and amplitude).

Some degree of control is provided based on the natural recruitment order of axons by size, proximity to the electrode and degree of myelination, but knowledge of the stimulus-response profiles of the respective fiber types is required if precision is needed. Stimulus-response profiles are not collected in most electrical nerve stimulation (ENS) applications, because they differ across patients, within the same patient over time, and require tedious stimulus-response measurements for each activation level of interest. Furthermore, the compound nerve action potential (CNAP) response magnitude is a function of the biology (e.g., neuron type, temperature and ion composition), electrode viability (e.g., increased impedance or thermal noise due to protein adsorption and glial encapsulation) and environmental influence (e.g., electrical noise and the effects of certain drugs or chemicals). An adaptive, closed-loop control system is needed to personalize the stimulation and resulting effect to each patient.

Regarding the approaches to control or study meurophysiology, Joseph Bergmans first introduced the principles and utility of measuring single motor axon activation thresholds. He showed that many of the inherent physiological properties of a single motor fiber is embodied in changes to its activation threshold. Generally speaking, an accurate estimate of the nodal membrane potential, which is largely a function of the voltage-gated receptor type, number and distribution, along with factors that influence their function, is inferred from changes in the nodal membrane activation threshold in response to experimental membrane polarization. The techniques developed by Bergmans were difficult to master, however, leaving his research at a standstill for several years. S A Raymond later introduced the "Threshold Hunter," a closed-loop circuit that clamps the probably of activation to 50% by dynamically adjusting the stimulus pulse duration. This tool significantly simplified the activation threshold measurement process first introduced by Bergmans.

Hugh Bostock and David Burke later introduced the "Threshold Tracker," a software tool that characterizes properties of the nodal membrane at the point of stimulation by processing measured changes in the activation threshold of a population of neurons within a nerve. The Threshold Tracker was designed to measure changes in motor neuron function due to "metabolic and toxic neuropathies"—factors that influence or degrade the integrity and function of the nodal membrane—but was later deemed suitable for the study of sensory neuron function. In contrast to the Threshold Hunter introduced by Raymond, the Threshold Tracker fixes pulse width and varies pulse amplitude to maintain a set level of nerve activation, as inferred from the magnitude of the evoked compound nerve or muscle action potential. The membrane properties of a particular neuron type are determined through activation changes brought about by various polarizing and hyperpolarizing stimuli paired with a stimulus pulse having a fixed duration and amplitude.

Vagus nerve stimulation (VNS) is a treatment alternative for many epileptic and depressed patients whose symptoms are not well managed with pharmaceutical therapy. Approximately 2-weeks after device implantation, a physician programs the pacemaker-like device to deliver intermittent pulses of current to the left cervical vagus nerve. The highest efficacy is typically observed after 1 year, but only after several minimally informed stimulus parameter adjustments. The efficacy of these treatments is far from optimal.

Over the course of weeks to months, a physician systematically tunes the stimulus until the patient and physician feel that the therapy is working with no adverse or intolerable side effects. If a bothersome side effect is encountered, the intensity of stimulation is decreased until the side effect disappears. These parameters are maintained until the next appointment. Major limitations beyond the subjective nature of this approach include 1) the risk of adaption or desensitization to the stimulus, which may make the therapy less effective over time (e.g., stimulus induced depression of neuronal excitability, or SIDNE), 2) the lack of feedback regarding the type and number of neurons that are activated when the therapy is effective, and 3) the risk of patient discomfort.

All ENS therapies use some form of a stimulus parameter-based dosing system. This is problematic, as stimulus parameters are poor predictors of therapeutic efficacy; each patient and nerve responds uniquely to the same strength of stimulation, and the relationship between stimulation and the degree of nerve activation changes over time. These factors limit treatment benefit and contribute to poorer efficacy on a shorter timescale. They also help to explain why the therapeutic mechanisms are not well understood despite decades of investigation. An objective, informed dosing system is required to improve the efficacy of ENS therapies and to further reduce the number and severity of side effects.

BRIEF SUMMARY

The present disclosure includes disclosure of sensory prosthesis devices and systems and methods of using the same, including, but not limited to, high-resolution, selective, and self-optimizing haptic and electrotactile displays and methods of using the same.

In an exemplary embodiment of a feedback system of the present disclosure, the feedback system comprises a prosthesis configured to be worn by an individual, the prosthesis comprising at least one prosthesis sensor configured to detect a state or condition in an environment of the at least one prosthesis sensor, and at least one actuator in communication with the at least one prosthesis sensor and configured to receive data relating to the detected state or condition and to stimulate a nerve of the individual; a neural sensor positioned upon or within the individual, the neural sensor configured to detect a neural response relating to the stimulation of the nerve by the at least one actuator; and a processor in communication with at least one of the at least one prosthesis sensor, at least one of the at least one actuator, and the neural sensor, the processor configured to control operation of the at least one actuator based upon the data relating to the detected state or condition from the at least one prosthesis sensor and data from a sensation map, the sensation map comprising sensation data relating to an experienced sensation from a brain of the individual in response to the neural response.

In an exemplary embodiment of a feedback system of the present disclosure, the at least one actuator is configured to directly stimulate the nerve of the individual.

In an exemplary embodiment of a feedback system of the present disclosure, the at least one actuator is configured to indirectly stimulate the nerve of the individual via skin of the individual.

In an exemplary embodiment of a feedback system of the present disclosure, the at least one actuator is configured to vibrate in response to the state or condition indicating vibration.

In an exemplary embodiment of a feedback system of the present disclosure, the at least one actuator comprises an array of actuators in communication with the processor via a plurality of signal pathways.

In an exemplary embodiment of a feedback system of the present disclosure, the system further comprises the sensation map, and the sensation data of the sensation map further relates to a second experienced sensation from the brain of the individual in response to a second neural response.

In an exemplary embodiment of a feedback system of the present disclosure, the system further comprises the sensation map, and the sensation data of the sensation map further relates to a plurality of additional experienced sensations from the brain of the individual in response to a corresponding plurality of neural responses.

In an exemplary embodiment of a feedback system of the present disclosure, the feedback system is accessible using a data processing system in communication with the feedback system, the data processing system comprising a data processor in communication with the feedback system, a data storage system, and a user interface system, wherein the data storage system is configured to store data processed by the data processor from the feedback system, and wherein the user interface system is configured to obtain inputs from a user to control operation of the data processor.

In an exemplary embodiment of a feedback system of the present disclosure, the data processor is controllable by a second data processing system in communication with the data processor through a network.

In an exemplary embodiment of a feedback system of the present disclosure, the actuator comprises a plunger positioned relative to an electromagnetic coil, the plunger having a tip configured to provide physical pressure to the nerve of the individual, the plunger configured for displacement from current flowing through the electromagnetic coil; a spring positioned relative to the plunger, the spring configured to oppose a force related to movement of the plunger; and a pressure sensor positioned relative to the spring, the pressure sensor configured to measure pressure provided by the plunger.

In an exemplary embodiment of a feedback system of the present disclosure, the actuator further comprises at least one heating element configured to stimulate the nerve of the individual with heat; and at least one cooling element configured to stimulate the nerve of the individual via cooling.

In an exemplary embodiment of a feedback system of the present disclosure, the plunger provides the physical pressure to the nerve of the individual in response to the detected state or condition from the at least one sensor and data from the sensation map relating to pressure.

In an exemplary embodiment of a feedback system of the present disclosure, the actuator stimulates the nerve of the individual with heat via operation of the at least one heating element in response to the detected state or condition from the at least one sensor and data from the sensation map relating to heat.

In an exemplary embodiment of a feedback system of the present disclosure, the actuator stimulates the nerve of the individual with cooling via operation of the at least one cooling element in response to the detected state or condition from the at least one sensor and data from the sensation map relating to cooling.

In an exemplary embodiment of a method of the present disclosure, the method comprises the steps of collecting sensor data from a sensor of a prosthesis; applying actuation via an actuator of the prosthesis corresponding to the sensor data to induce a neural response from a nerve of an individual wearing the prosthesis; measuring the neural response from the individual; receiving data of a sensation corresponding to the neural response; generating a sensation map relating the sensor data to the data of the sensation; and repeating the collecting, applying, measuring, receiving, and generating steps to generate a comprehensive sensation map corresponding to the sensor.

In an exemplary embodiment of a method of the present disclosure, the sensor data and the data of the sensation within the comprehensive sensation map is used to further apply actuation of the actuator by way of movement of a plunger of the actuator to provide physical pressure to the nerve of the individual in response to the sensor data and the data of the sensation indicating pressure from the sensor of the prosthesis.

In an exemplary embodiment of a method of the present disclosure, the sensor data and the data of the sensation within the comprehensive sensation map is used to further apply actuation of the actuator by way of operation of at least one heating element of the actuator to provide heat to the nerve of the individual in response to the sensor data and the data of the sensation indicating heat from the sensor of the prosthesis.

In an exemplary embodiment of a method of the present disclosure, the sensor data and the data of the sensation within the comprehensive sensation map is used to further apply actuation of the actuator by way of operation of at least one cooling element of the actuator to provide cooling to the nerve of the individual in response to the sensor data and the data of the sensation indicating cooling from the sensor of the prosthesis.

In an exemplary embodiment of an actuator configured for use with a prosthesis configured to be worn by an individual of the present disclosure, the actuator comprises a plunger positioned relative to an electromagnetic coil, the plunger having a tip configured to provide physical pressure to a nerve of the individual, the plunger configured for displacement from current flowing through the electromagnetic coil; a spring positioned relative to the plunger, the spring configured to oppose a force related to movement of the plunger; a pressure sensor positioned relative to the spring, the pressure sensor configured to measure pressure provided by the plunger; at least one heating element configured to stimulate the nerve of the individual with heat; and at least one cooling element configured to stimulate the nerve of the individual via cooling; wherein operation of the actuator is controlled using a processor in communication with the actuator, the processor configured to control operation of the actuator based upon data obtained by a sensor of the prosthesis and a sensation map comprising sensation data relating to an experienced sensation from a brain of the individual.

In an exemplary embodiment of an actuator configured for use with a prosthesis configured to be worn by an individual of the present disclosure, the actuator is configured to a) provide the physical pressure based upon pressure data obtained by the sensor of the prosthesis, b) provide the heat based upon heat data obtained by the sensor of the prosthesis, and c) provide the cooling based upon cooling data obtained by the sensor of the prosthesis.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIG. 8 shows a graphical representation of an example user interface (UI) for receiving from a user data of intensities of various sensations, e.g., for classifying sensations.

FIGS. 10C-10D show examples of classifications of nerves, according to exemplary embodiments of the present disclosure;

FIG. 12D shows data from the left cervical vagus nerve of a rat, according to an exemplary embodiment of the present disclosure;

Figure 1:
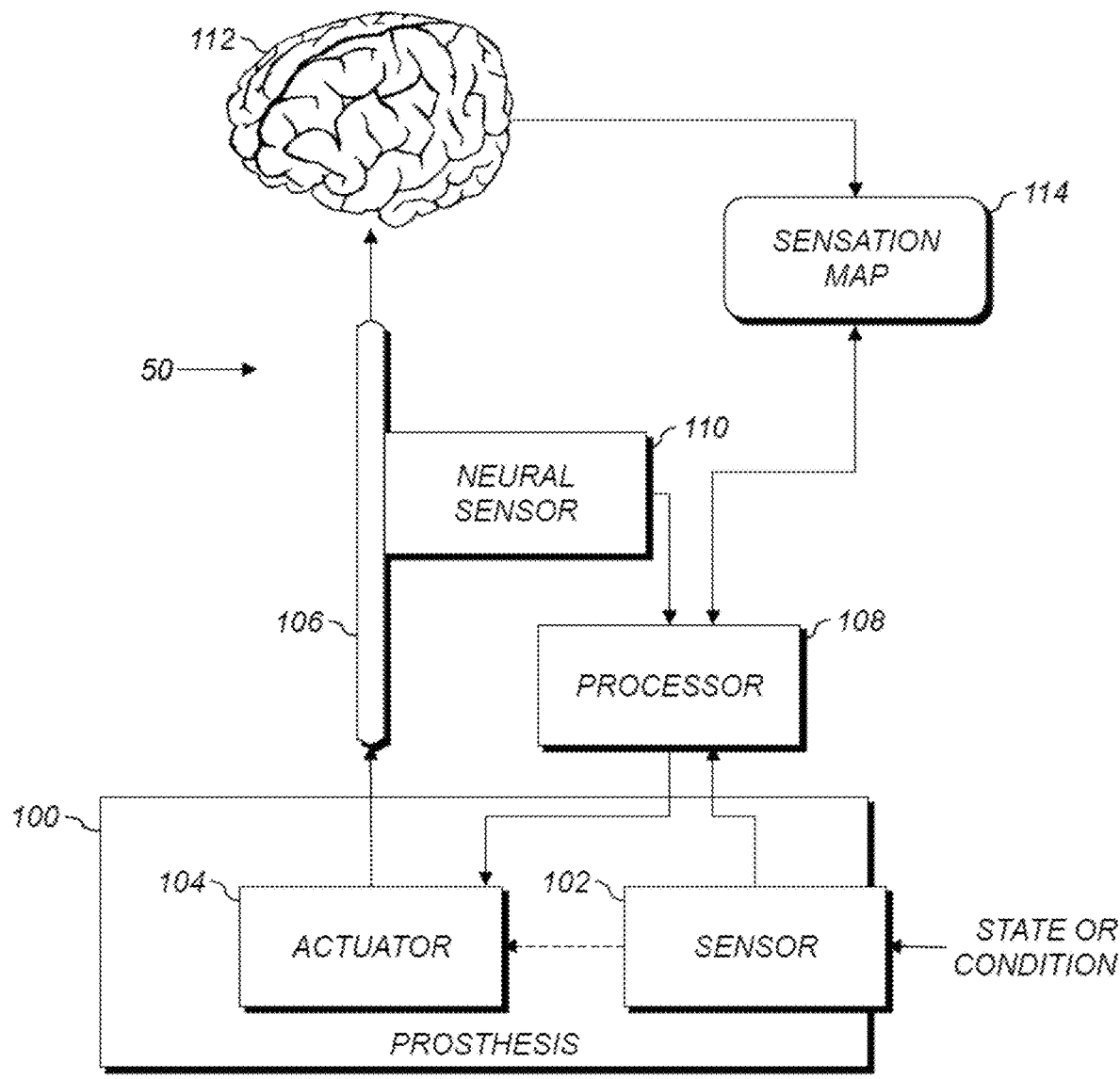
FIG. 1 shows a block diagram of a system, according to an exemplary embodiment of the present disclosure.

The attached drawings are for purposes of illustration and are not necessarily to scale.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended. The terms "I," "we," "our" and the like which may be referenced herein do not refer to any specific individual or group of individuals.

Throughout this description, some aspects are described in terms that would ordinarily be implemented as software programs. Those skilled in the art will readily recognize that the equivalent of such software can also be constructed in hardware, firmware, or micro-code. Because data-manipulation algorithms and systems are well known, the present description is directed in particular to algorithms and systems forming part of, or cooperating more directly with, systems and methods described herein. Other aspects of such algorithms and systems, and hardware or software for producing and otherwise processing signals or data involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

The present disclosure includes disclosure of autonomous neural control (ANC), a nerve activation control system designed to eliminate patient response variability and the detrimental effects of the foreign body response at the device-tissue interface. In rats, ANC rapidly learns how to most efficiently activate any proportion of vagal A, B, and/or C fibers over time. It provides a new dosing mechanism based on neural activation. In real time, ANC systematically decodes evoked compound nerve action potential (CNAP) responses to construct a patient-specific nerve activation profile (NAP), which describes how each neuron population in the nerve will respond to any strength of stimulation. Over the course of ENS therapy, ANC continuously refines the NAP to improve its prediction accuracy and adapt to circadian, drug-induced, or immune mediated changes at the device-tissue interface.

ANC refines the electrical stimulus, within safe limits, to selectively control nerve activation on a patient-to patient, nerve-to-nerve and neuron-to-neuron basis. By providing consistent nerve activation, ANC allows reproducible experiments to systematically delineate the therapeutic mechanisms of VNS or other form of ENS therapy. Furthermore, biological markers of treatment response may be measured and classified with respect to the NAP, simplifying the development of fully personalized, closed-loop control systems for treating diverse neurological diseases.

For physicians, ANC will 1) establish an objective, standardized dosing system based on the level of nerve/neuron activation or inhibition, expressed as a percentage of maximal nerve/neuron activation, 2) eliminate the complicated, time consuming stimulus parameter tuning process, 3) provide a simple mechanism to adjust the relative ratios of A, B and C fiber activation, and 4) ensure that therapeutic nerve/neuron activation is maintained over time. For patients, ANC can 1) improve efficacy and enhance the overall quality of ENS therapy, 2) reduce the number of doctor visits, and 3) help extend device lifetime by reducing energy waste from excessive stimulation.

Prostheses and systems according to various aspects herein can restore sensation through a lost limb (e.g., an amputated arm) in a way that feels natural to the user (e.g., the amputee). Various prior prostheses lack sensory feedback. Various prior prostheses stimulate neurons but lack day-to-day usability; for example, some prior prostheses require daily calibration. Various prior schemes use sensors and transceivers for which placement may vary from day to day, and are negatively affected in their performance by variations over time in the electrical sensitivities of the user's nerves.

Various aspects herein infer sensory feedback at a patient's brain by measuring nerve impulses. Various aspects measure and classify nerve response. Various aspects use machine-learning techniques to provide electrical stimuli that match user-identifiable sensations. Various aspects adjust stimulus to the nerves in a closed-loop manner to provide a desired nerve response. Various aspects can work with existing sensors or electrodes, e.g., implantable sensors positioned proximal to nerves or external sensors placed on the skin. Implantable sensors can be positioned, e.g., upstream of a stimulator, anywhere between the brain and stimulator. As used in this document, "upstream" refers to the afferent direction, i.e., travel towards, or proximity to, the brain; "downstream" refers to the efferent direction, i.e., travel away from, or distance from, the brain.

Various nerves are "mixed nerves." For example, the medial, radial, and ulnar nerves are mixed nerves, i.e., carry motor and sensor information bidirectionally on the same nerve. Different ones of these nerves enervate different portions of the user's hand. Various aspects stimulate more than one of these nerves simultaneously on concurrently to provide a specific pattern of nerve actuation or sensation. Various examples use a single interface for multiple nerves. Various aspects use a single interface for both sensing via, and actuation of, prosthetic elements.

FIG. 1 shows a block diagram of an exemplary feedback system 50 of the present disclosure. In various embodiments referenced herein, system comprises a prosthesis 100, e.g., a robotic arm, including one or more sensors 102 that detect state(s) or condition(s) in the environment. Sensors 102, as referenced herein, can effectively and artificially introduce sensations to neural sensors 110, as referenced herein, via operation of actuator(s) 104. Actuators 104, e.g., in the prosthesis 100 or elsewhere on the user's body, stimulate nerves 106 according to the detected state(s) or condition(s), e.g., under control of processor 108, discussed below. Actuators 104 can stimulate the nerves 106, e.g., directly or via the skin, as discussed below. The term "actuator" does not require that any actuator 104 cause or bring about any motion.

Neural sensors 110, e.g., implantable sensors, detect neural response(s) corresponding to the actuation and can provide those to processor 108 and/or 286 or another device that operates a control loop. In some examples, a neural sensor 110 includes a small, particularly-shaped piece of metal that picks up signals from proximal or adjacent nerves 106.

An exemplary prosthesis 100, as referenced herein, may also be referred to herein as an advanced robotic arm, with the robotic arms of the present disclosure differing from other robotic arms known in the art for at least the reason that the prosthesis 100 embodiments of the present disclosure are able to sense/detect information from the environment and from the limb portion of the wearer of said prosthesis 100. As discussed in detail herein, various signals from the brain 112 or nerves 106 are utilized as data within a sensation map 114, so to provide feedback back to prosthesis 100. Prosthesis 100 embodiments of the present disclosure can therefore effectively replace lost limb function, as referenced herein.

Figure 16:
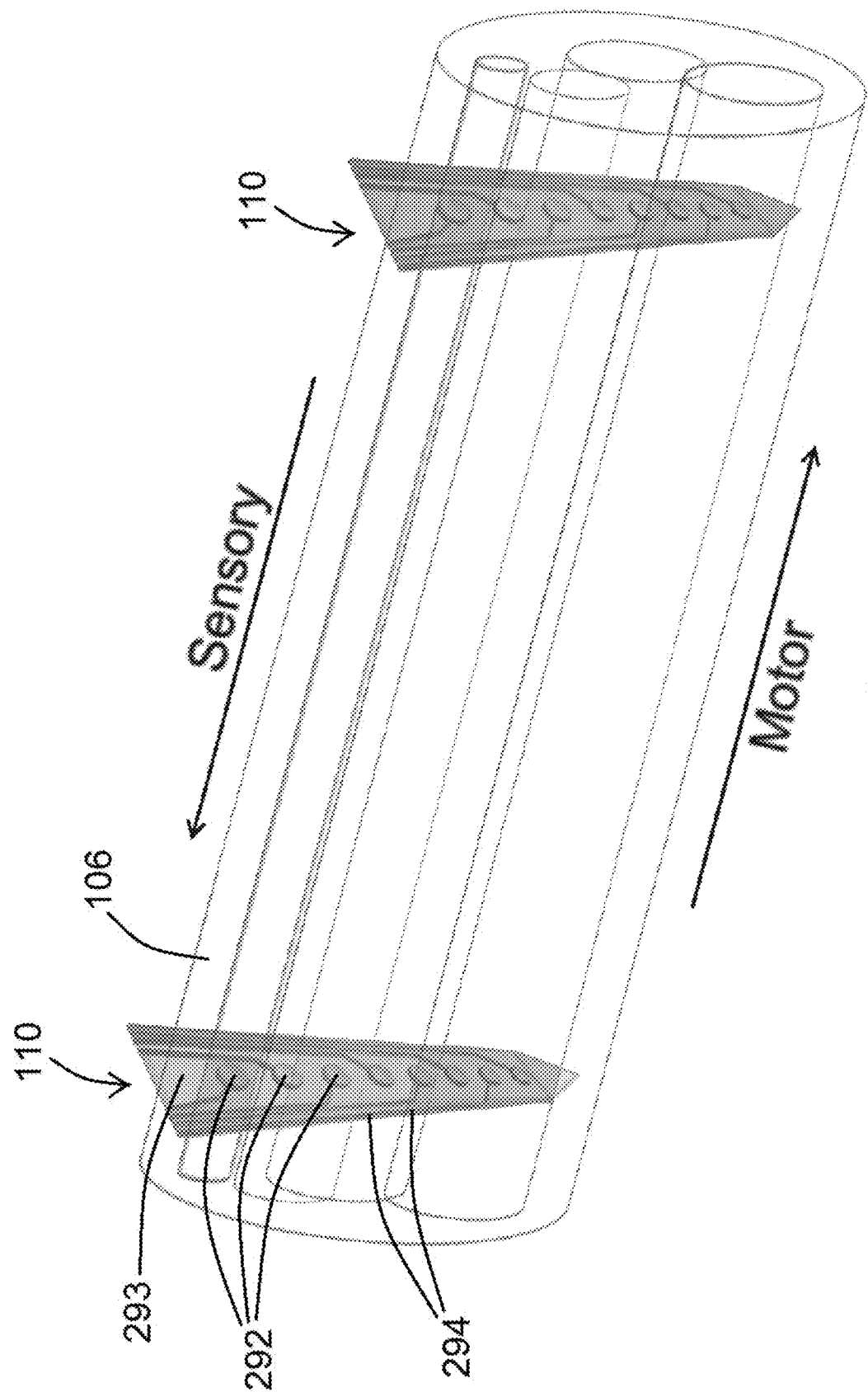
FIG. 16 shows an example nerve structure indicating nerve stimulus as well as measurement of nerve response, according to an exemplary embodiment of the present disclosure.

In some examples, readings from neural sensors 110 are used to adjust the operation of actuators 104 in a closed control loop to provide a desired (e.g., stored or predetermined) neural response. The neural response travels to the user's brain 112, where the user experiences a corresponding sensation. The user can provide sensation data during a training process, as described below, to permit processor 108 or 286 to provide neural stimuli corresponding to output(s) of sensor(s) 102. The training process can provide, produce, generate, supplement, and/or modify sensation map 114 as an output. Neural sensors 110, as referenced herein and as shown in FIGS. 1 and 16, for example, can comprise high-density electrodes 292 that are effectively implanted in or onto nerves 106 within the body so to operate as referenced herein. As shown in FIG. 16, for example, electrodes 292 can be positioned upon or within a substrate 293, and connected to one another and/or to other elements of systems 50, 201 via one or more wires or traces 293. Directions for sensory information and motor information are reflected via the arrows shown in FIG. 16.

For example, in a right-hand or right-arm prosthesis 100, when sensor 102 detects pressure corresponding to a handshake, processor 108 or 286 can adjust operate actuators 104 based on sensation map 114 to provide the user with the experience, e.g., sensation(s), of feeling the hand of the person shaking the user's hand. In some examples, sensors 102 include, e.g., a fingertip pressure sensor 102 with a calibrated response from the pressure on the sensor 102 to the electrical output of that sensor 102. The processor 108 can then use the sensation map 114 to determine the neural response corresponding to selected pressures on the sensor 102, and provide corresponding stimulation to the nerves 106 via the actuators 104. This permits assigning user meaning to specific inputs from sensors 102. Various examples include a sensorized robotic arm (prosthesis 100) with known sensor 102 response curves.

The processor 108 is shown outside prosthesis 100 but can be included therein. One processor 100 can correspond to one or more prostheses 100, sensors 102, or actuators 104. Any number of processors 108 can be used to operate a given prosthesis 100, sensor 102, or actuator 104. The inputs from any number of sensors 102 can be processed by processor 108 to determine the output for a single actuator 104. The input from a single sensor 102 can be processed by processor 108 to determine the output for any number of actuators 104. Processor 108, in various embodiments, is configured to control operation of actuator 104, as referenced herein.

In some examples, other biological sensors are used in place of neural sensor 110. For example, galvanic skin response, heart rate, blood chemistry, or other biological parameters can be used as proxies for nerve response. As such, in embodiments of systems 50 referenced herein that utilize a neural sensor 110, such embodiments can instead utilize one or more other parameters measurable from the patient in lieu of said neural sensor(s).

In some examples using cutaneous stimulation, actuators 104 stimulate the skin surface on patients with nerves 106 re-routed to pectoral muscles. The nerves 106 can be surgically re-routed to create a map of the hand on the pectoral muscles, i.e., a mapping between locations on the muscle and locations on the hand. These aspects can permit restoring sensation via the skin surface corresponding to the re-routed nerves 106. In some examples, the skin surface is stimulated and the nerve 106 response measured.

In some examples, the particular type of any given neuron (nerve 106) being measured is determined from the response of that neuron. For example, axon diameter is positively correlated with speed of impulse travel. Moreover, different nerves have different, measurable activation thresholds.

Various aspects determine relationships between stimulus (e.g., electrical or skin stimulus) and neural response, and between neural response and user sensation. Various aspects combine these determined relationships to determine relationships between stimulus and user sensation, e.g., from stimulus to sensation or from sensation to stimulus. Various aspects use a determined mapping from sensation to stimulus to determine the stimulus for a sensation corresponding to a condition or state detected by a sensor 102 on a prosthesis 100, e.g., heat or pressure. Various aspects then apply the determined stimulus to the user's nerves 106 (e.g., directly or via a cutaneous or other actuator 104, and likewise throughout) to provide the user with a simulation of directly experiencing the condition or state via the senses.

As referenced in FIG. 1, system 50 provides for bidirectional feedback between components of prosthesis 100 and other elements of system 50, such as neural sensor 110, processor 108, and/or sensation map 114 and data contained therein. Various subjective descriptors can comprise data contained within sensation map 114, relating to various experienced sensations from the user's brain 112. The self-training algorithms referenced herein are used to close the feedback loop referenced herein, relating inputs from sensors 102 of the prosthesis 110 to electrodes within neural sensor 110, for example, so to effectively link nerve 106 responses and patterns of nerve activity to sensation.

To determine the mapping from stimulation to neural response, neural sensors 110 are used to measure neural response under various conditions of stimulation. This can be done during the training process described below.

To determine the mapping from neural response to user sensation, a machine-learning algorithm or other training process is used. The user's nerves are stimulated with various levels and types of stimulation is presented with various stimulations. The user provides data on what sensation the user perceived and how intense the sensation was. Example sensations and level ranges are described herein and shown, e.g., in FIGS. 8 and 11. For example, levels can range from 0 (no sensation) to 9 (the strongest sensation of that type the user can image). The user-provided sensation data can be clustered, smoothed, or otherwise postprocessed to form the sensation map 114. In some examples, training is a non-real-time input to a prosthetic system and nerve responses are a real-time input to the system.

In some examples, a user goes through a training process for each sensor 102. In some examples, the sensation map 114 is stored and can be used for a user-selectable, amount of time, e.g., as long as the user is comfortable with the sensations produced by actuation of sensor 102. In some examples, the training process includes monitoring sensor 102 and neural sensor 110 outputs while the user performs actions such as everyday tasks. The user can provide sensation data while performing the tasks, and the sensation map 114 can be adjusted in realtime until the user indicates that the sensations associated with the task are acceptable (e.g., whether or not "it feels right"). The training process can be used with any number or combination of sensors 102 and actuators 104, e.g., HETDisp actuators discussed below or conventional pressure or temperature sensors or other actuators.

Figure 17:
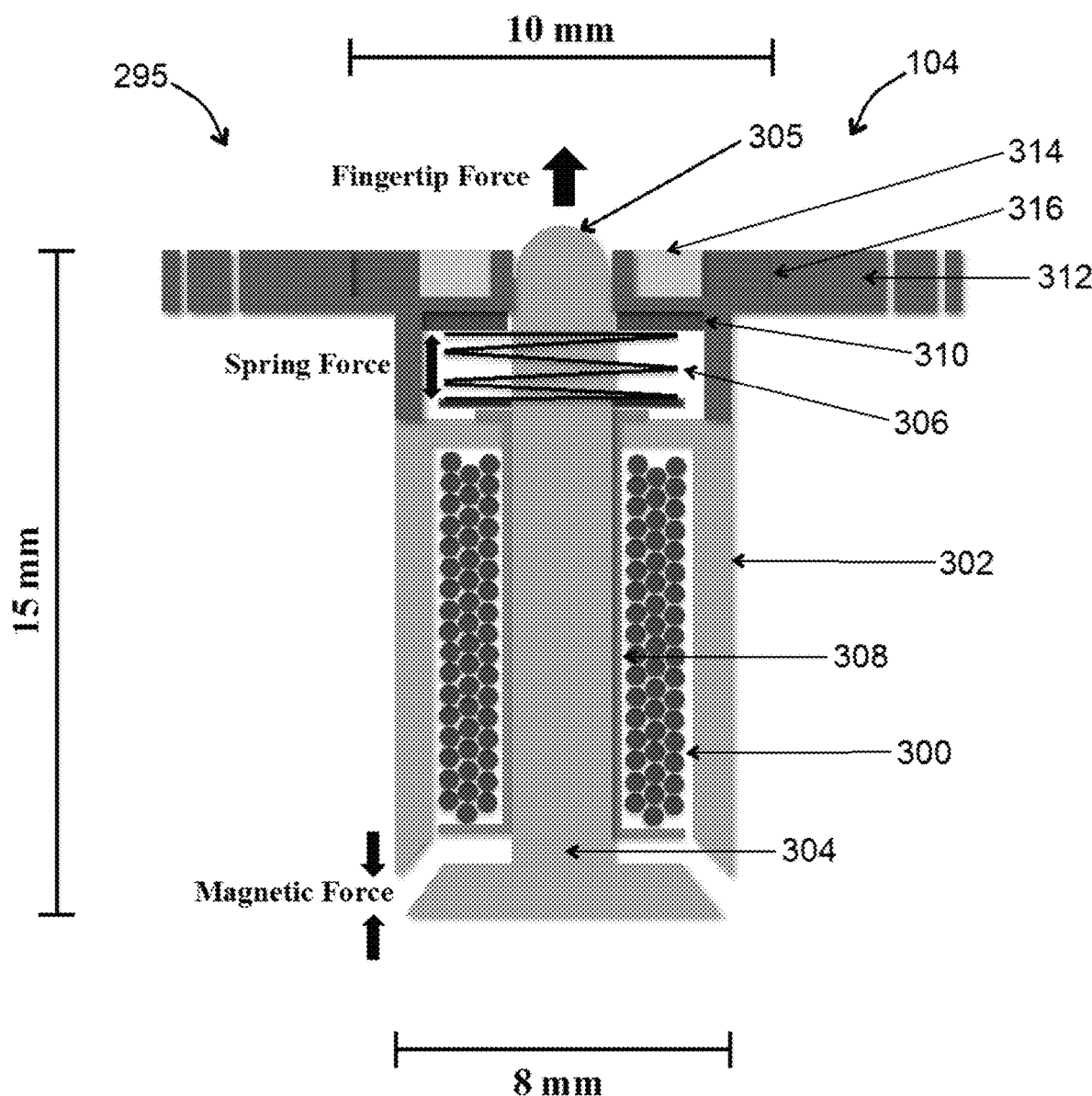
FIG. 17 shows an elevational cross-section of an actuator, according to an exemplary embodiment of the present disclosure.
Figure 18:
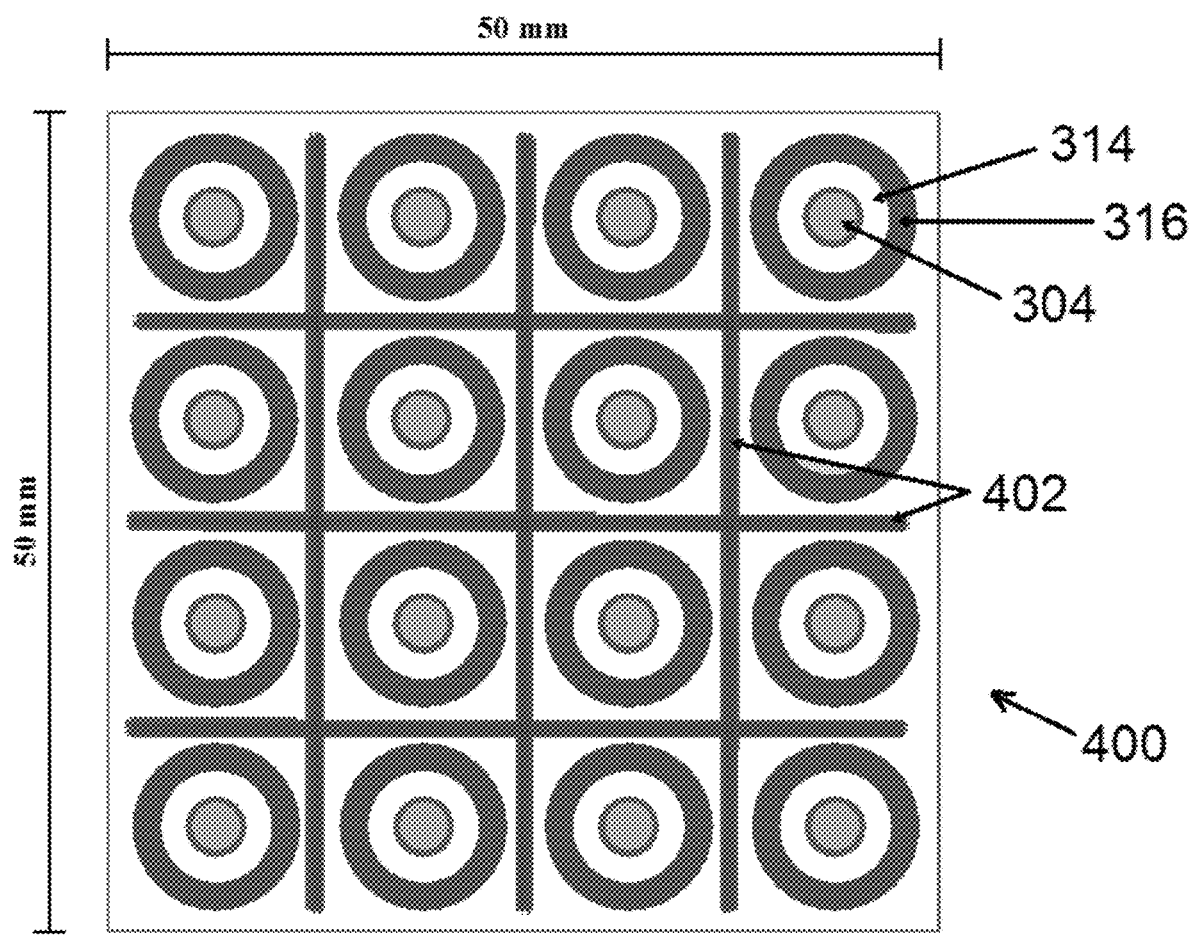
FIG. 18 shows a plan view of an actuator array, according to an exemplary embodiment of the present disclosure.

FIGS. 17 and 18 show examples of an actuator 104 ("HETDisp"), according to various aspects, including a moveable element, e.g., a vibratory element (a plunger 304, as referenced in further detail herein), that is electrically conductive. This permits the vibratory element (here, the plunger 304) to be used for skin pressure actuation and electrical stimulation, e.g., of sticking or other surface friction characteristics. The HETDisp also includes heating elements 316 and/or cooling elements 314 that can provide sensations of hot and cold. Any combination of electrical, vibratory, heating, and cooling actuations can be provided concurrently or sequentially to produce desired nerve responses. The heating and cooling elements 316, 314 are examples of heat sources and heat sinks, respectively. In some examples, a thermoelectric element or other device is used that can selectively heat or cool (a "heat source/sink").

In some examples, a plurality of actuators 104 are arranged in a patch (also referred to herein as an array 400) over a portion of the user's body, e.g., in a matrix arrangement. The actuators 104 can be controlled using passive-matrix or active-matrix display strategies commonly used in softcopy displays. The matrix (array 400) of actuators 104 can include any number or combination of HETDisp or prior actuators 104, and can be a single row or column. Actuators 104 are not constrained to lie along a straight line.

At least FIGS. 3, 4, 6 and 7 show exemplary data of cutaneous hindpaw stimulation in rodents. A tuning curve was determined to map stimulation to neural response, and is shown.

Various aspects of the present disclosure provide a scalable, high-resolution and self-optimizing haptic and electro-tactile display (e.g., actuator matrix) that provides sensory feedback to a user through custom software-guided, patterned electrical stimulation of mechanoreceptors and proprioceptors, in isolation or combination, through the skin or an implantable interface, using dense arrays of electrodes, in isolation or in combination, with components commonly used in haptic (vibrating) displays and digital (visual) displays. The technology solves challenges faced by previous attempts at designing realistic, usable haptic and electro-tactile displays, namely a lack of day-to-day reproducibility, an inability to reproduce realistic multi-component sensory stimuli in users of the device(s), and an inability to scale the technology.

Various aspects provide a scalable, high-resolution and self-optimizing haptic and electro-tactile display that provides sensory feedback to a user through custom software-guided, patterned electrical stimulation of mechanoreceptors and proprioceptors, in isolation or combination, through the skin or an implantable interface, using dense arrays of electrodes, in isolation or in combination with components commonly used in haptic (vibrating) displays and digital (visual) displays. The technology solves challenges faced by previous attempts at designing realistic, usable haptic and electro-tactile displays, namely a lack of day-to-day reproducibility, an inability to reproduce realistic multi-component sensory stimuli in users of the device(s), and an inability to scale the technology.

Applications of this technology are numerous. A non-comprehensive list is: Sensory restoration, Remote surgery, Sensory substitution, Exposure therapy, Rehabilitation therapy, Cognitive behavioral therapy, iPhysical therapy, Virtual reality, Aviation, Navigation, Stealth communication, Consumer electronics, Marketing, Apparel, Navigation., Virtual reality. Various aspects relate to electro-tactile displays, haptic displays, electrocutaneous stimulation, sensory restoration, or selective mechanoreceptor recruitment.

Various aspects of training procedures herein can be used with haptic actuators that use grids of vibrating elements to induce a sensation in a user, or with electro-tactile technology including, e.g., high-speed switching networks and new electrode or stimulation topologies, or mechanoreceptor activation in isolation versus in combination. Various aspects herein provide improved day-to-day usability (e.g., do not require intensive calibration on a day-to-day or hour-to-hour basis, such as accounting for changes in skin impedance with additional support circuitry). Various aspects herein provide an interface that improves its performance on a day-to-day basis (i.e., it does not require re-calibration on a day-to-day basis). Various algorithms herein work with external or implantable haptic, electro-tactile, or combination haptic/electro-tactile interfaces, e.g., combination haptic/electro-tactile devices/displays. Various aspects are scalable in terms of cost, the type and intensity of a sensation, and the resolution of a sensation.

Various aspects predict a sensation that a user might experience using a particular combination of stimulus parameters using relationships between a physiological response, such as a nerve signal, the parameters of stimulation, and the subjective input from a user. This was described above with reference to the sensation map 114.

Various aspects correlate a subjective experience of a sensation and the hardware/software that evokes the sensation. Various aspects learn patterns of stimulation/output that induce a very specific sensation in a user, sensations that can only be understood as real by the user, e.g., due to previous experiences of the sensation in a natural manner.

Various aspects are useful in sensory restoration interfaces for patients with missing limbs.

Steps of various methods described herein can be performed in any order except when otherwise specified, or when data from an earlier step is used in a later step. Exemplary method(s) described herein are not limited to being carried out by components particularly identified in discussions of those methods.

In view of the foregoing, various aspects provide neural stimulation. A technical effect is to measure physical properties of a user's environment and provide the user corresponding sensations, e.g., in place of the sensations the user would have received from a limb had it been present.

Figure 2:
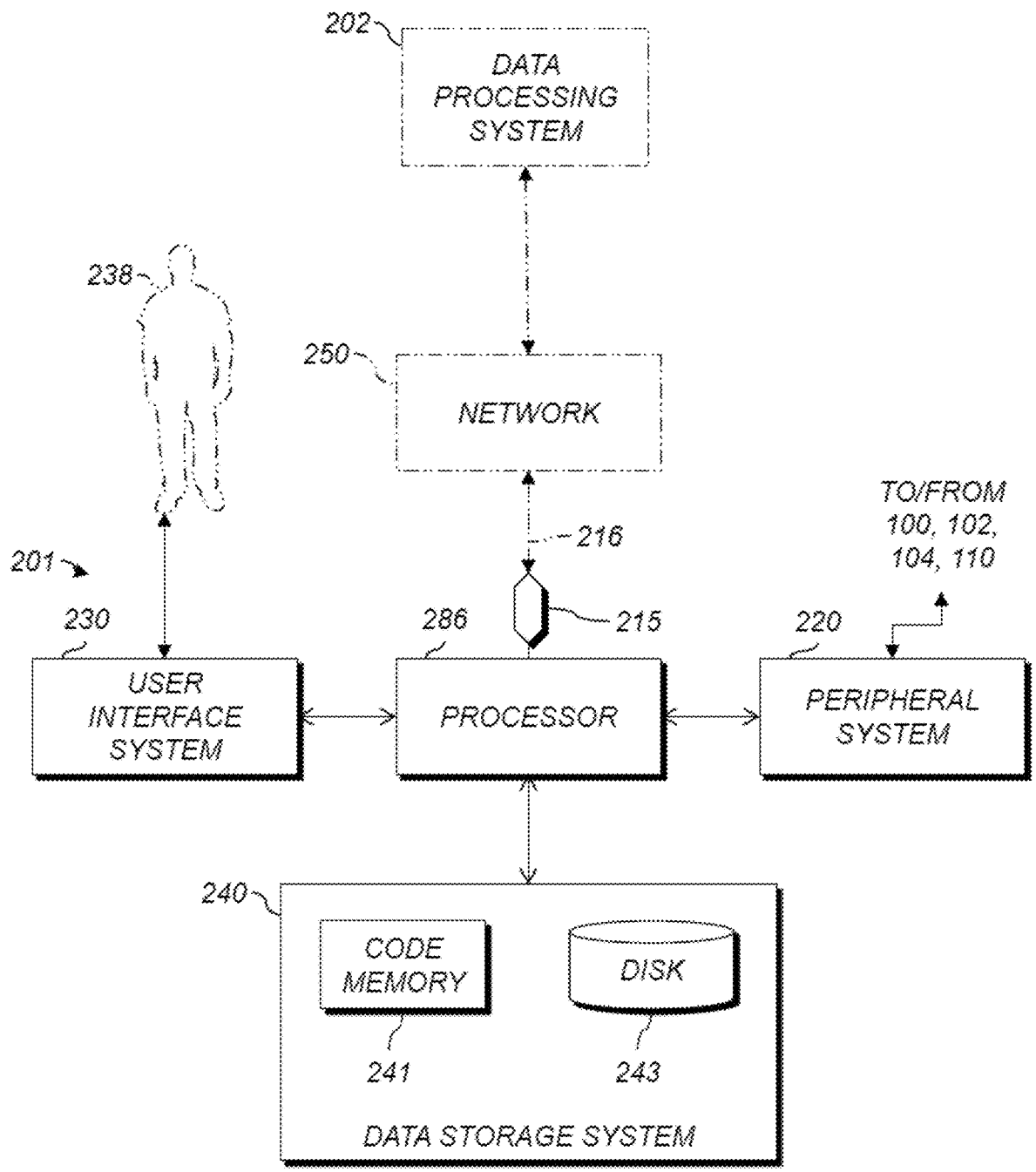
FIG. 2 is a high-level diagram showing the components of a data-processing system, according to an exemplary embodiment of the present disclosure.
Figure 3:
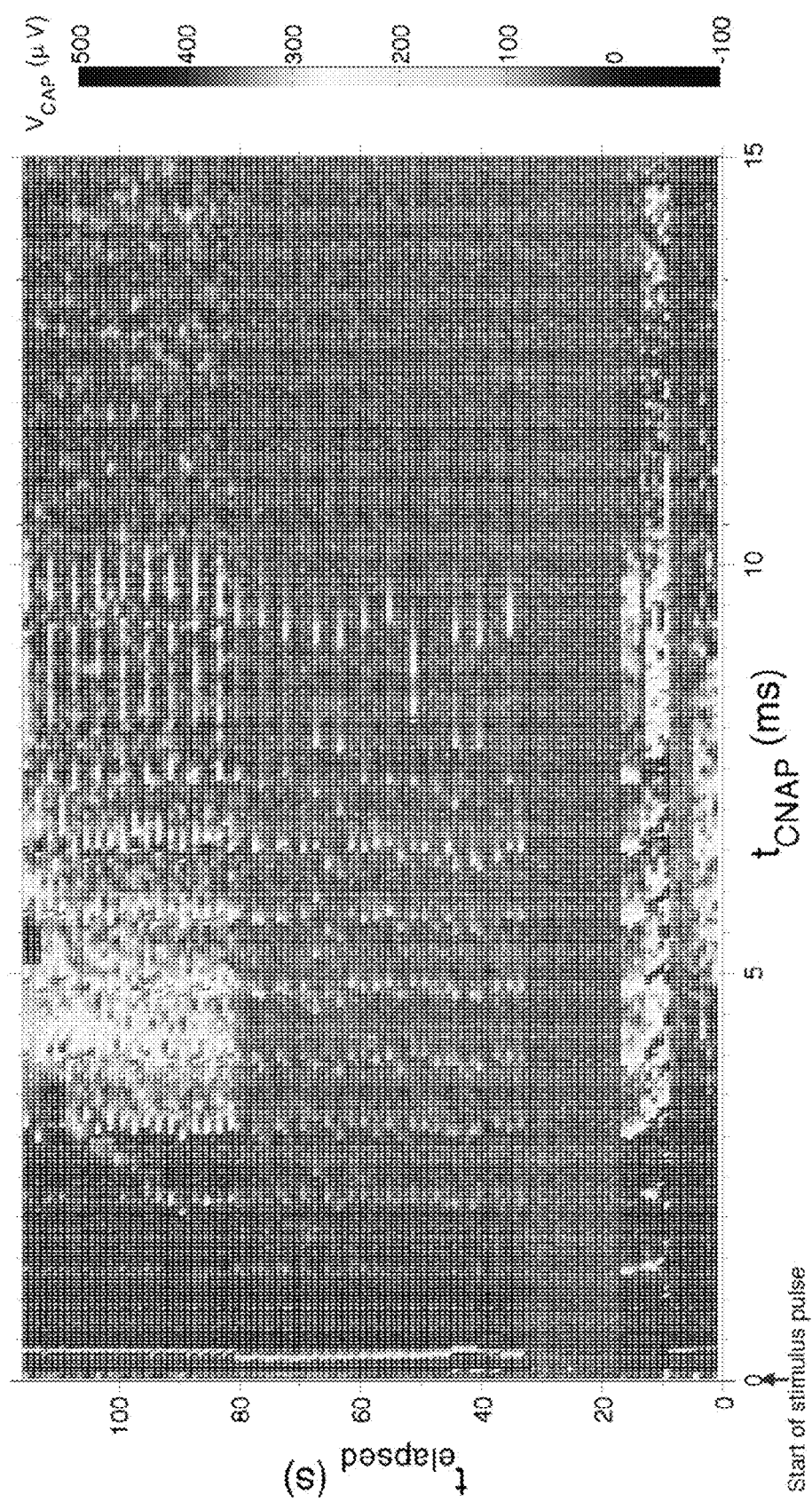
FIG. 3 shows a top-down view of FIG. 6, according to an exemplary embodiment of the present disclosure.
Figure 4:
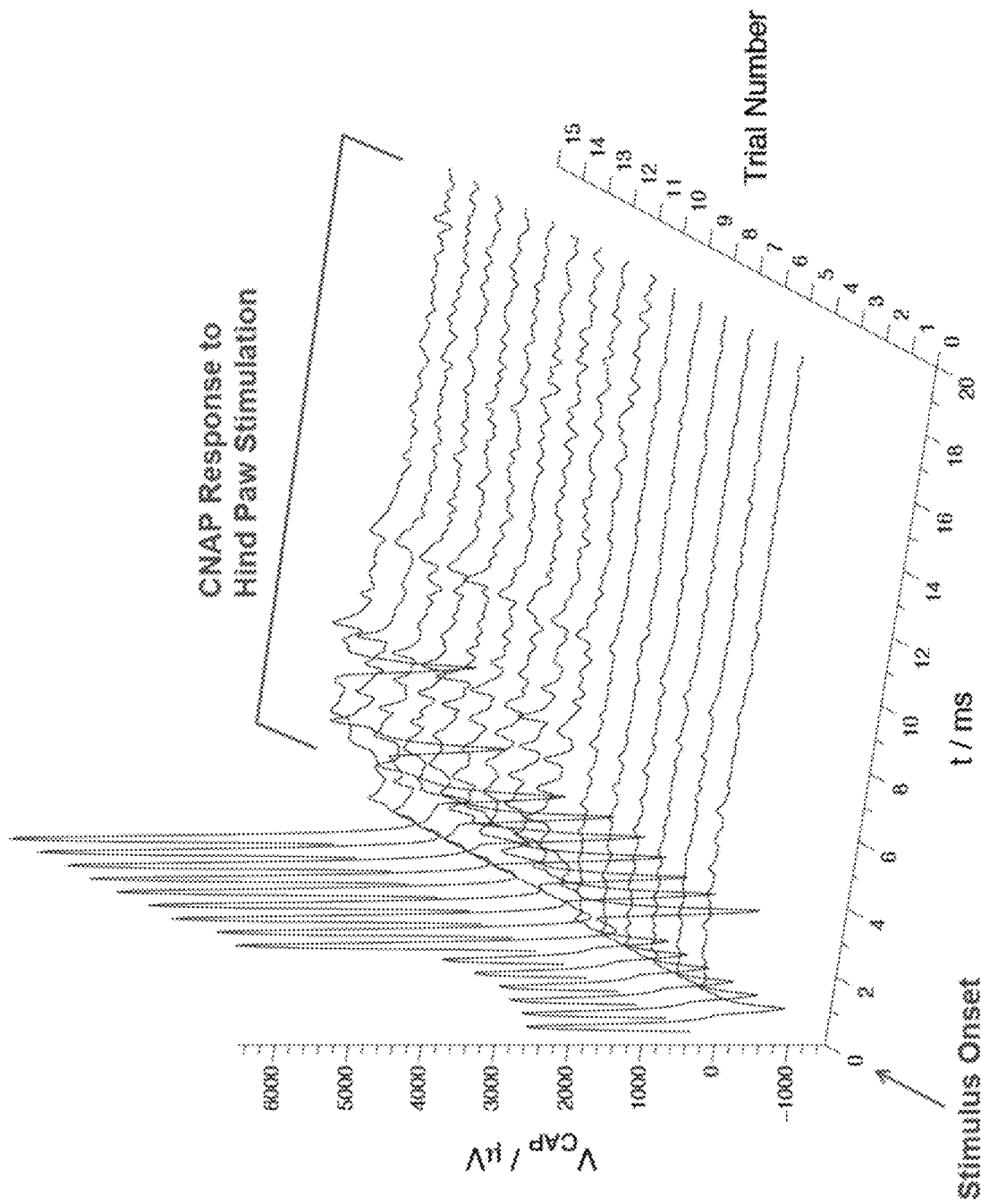
FIG. 4 shows exemplary experimental data of the present disclosure. The CNAP recording location was the left sciatic nerve. The stimulus location was the left hind paw (pad). The stimulus type was constant-current, cathode-first, alternating monophasic stimulation. Qst/phase increases with Trial Number. Each trace is a mean of N=4 CNAP responses.

FIG. 2 is a high-level diagram showing the components of an exemplary data-processing system 201 for analyzing data and performing other analyses described herein, and related components. The system 201, as shown in FIG. 2, includes a processor 286, a peripheral system 220, a user interface system 230, and a data storage system 240. The peripheral system 220, the user interface system 230 and the data storage system 240 are communicatively connected to the processor 286 and/or processor 108, shown in FIG. 1. Processor 286 can be communicatively connected to network 250 (shown in phantom), e.g., the Internet or a leased line, as discussed below. Prosthesis 100, sensor 102, actuator 104, processor 108, or neural sensor 110 can each include one or more of processor 286 and/or systems 220, 230, and/or 240, and can each connect to one or more network(s) 250. Processor 286, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Processor 286 can implement processes of various aspects described herein, e.g., training processes. Processor 286 and related components can, e.g., carry out processes for reading sensors 102, operating actuators 104, running closed- or open-loop control laws, and/or determining sensation maps 114, for example.

Processors 286 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise.

The phrase "communicatively connected" includes any type of connection, wired or wireless, for communicating data between devices or processors. These devices or processors can be located in physical proximity or not. For example, subsystems such as peripheral system 220, user interface system 230, and data storage system 240 are shown separately from the data processing system 286 but can be stored completely or partially within the data processing system 286.

The peripheral system 220 can include or be communicatively connected with one or more devices configured or otherwise adapted to provide digital content records to the processor 286 or to take action in response to processor 186. For example, the peripheral system 220 can include digital still cameras, digital video cameras, cellular phones, or other data processors. The processor 286, upon receipt of digital content records from a device in the peripheral system 220, can store such digital content records in the data storage system 240. The peripheral system 220 can be communicatively connected with prosthesis 100, sensor 102, actuator 104, processor 108, and/or neural sensor 110, devices shown in FIGS. 17 and 18, or components of any of those elements.

Figure 8:
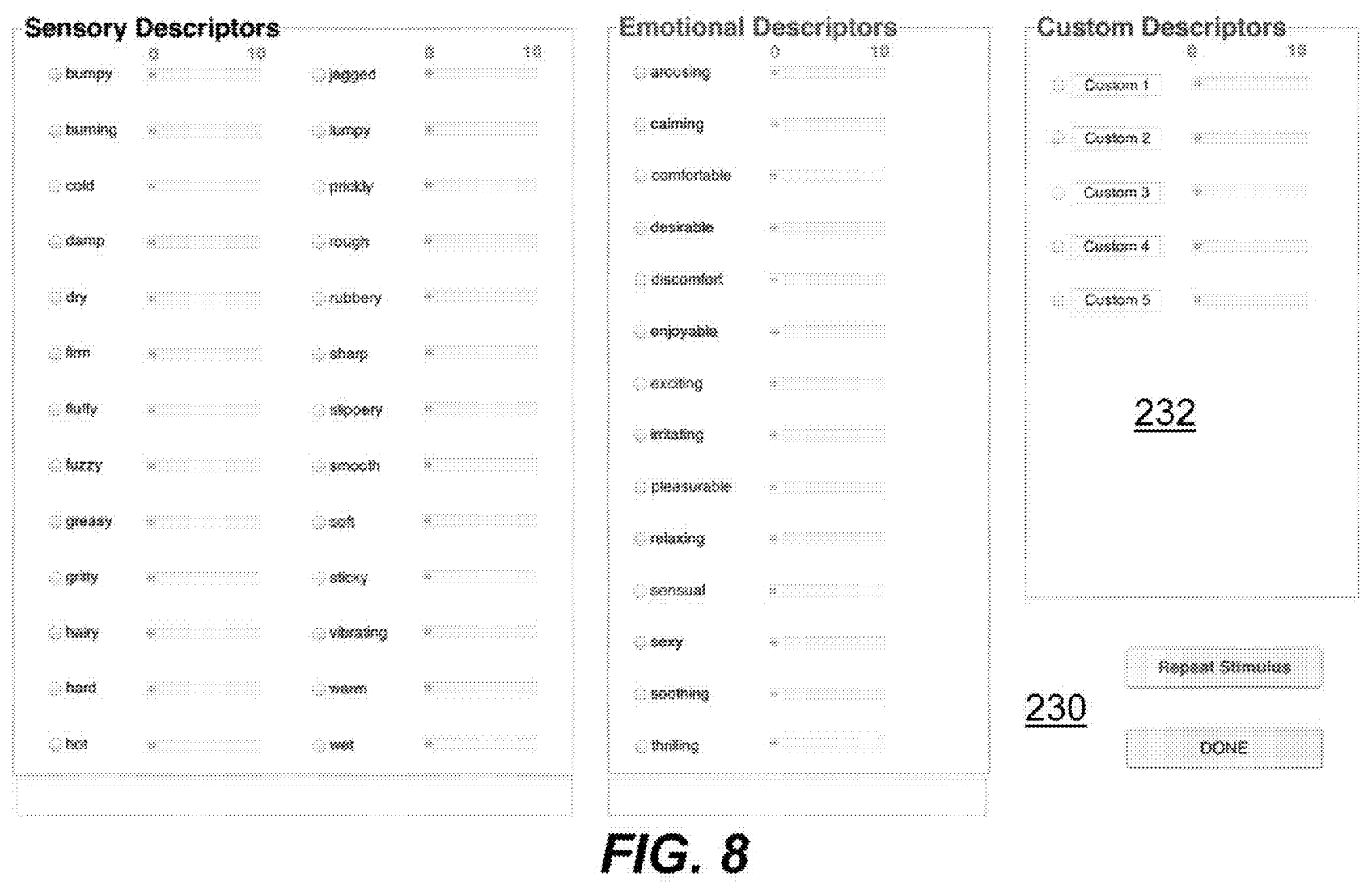
Figure 11:
FIG. 11 shows an example UI for classifying sensations used with a handheld electronic device, according to an exemplary embodiment of the present disclosure.
Figure 15:
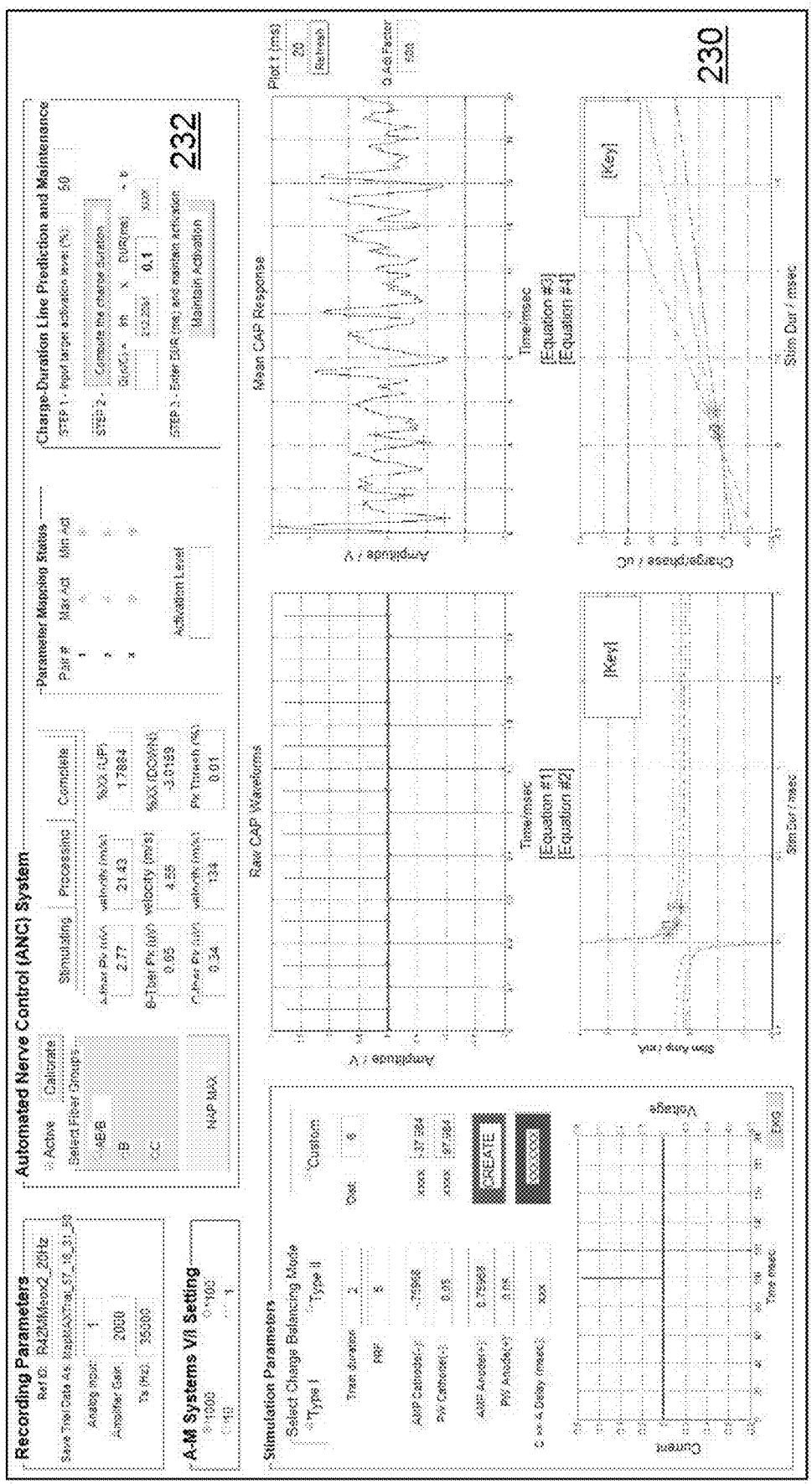
FIG. 15 graphically represents a graphical UI for autonomous neural control, according to an exemplary embodiment of the present disclosure.

The user interface system 230 can convey information in either direction, or in both directions, between a user 238 and the processor 286 or other components of system 201. The user interface system 230 can include a mouse, a keyboard, another computer (connected, e.g., via a network or a null-modem cable), or any device or combination of devices from which data is input to the processor 286. The user interface system 230 also can include a display device, a processor-accessible memory, or any device or combination of devices to which data is output by the processor 286. The user interface system 230 and the data storage system 240 can share a processor-accessible memory. Example user interfaces 232 that can be provided by user interface system 230 are illustrated in FIGS. 8, 11, and 15.

In various aspects, processor 286 includes or is connected to communication interface 215 that is coupled via network link 216 (shown in phantom) to network 250. For example, communication interface 215 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WIFI or GSM. Communication interface 215 sends and receives electrical, electromagnetic or optical signals that carry digital or analog data streams representing various types of information across network link 216 to network 250. Network link 216 can be connected to network 250 via a switch, gateway, hub, router, or other networking device.

In various aspects, system 201 can communicate, e.g., via network 250, with a data processing system 202, which can include the same types of components as system 201 but is not required to be identical thereto. Systems 201, 202 are communicatively connected via the network 250. Each system 201, 202 executes computer program instructions to perform functions described herein.

Processor 286 can send messages and receive data, including program code, through network 250, network link 216 and communication interface 215. For example, a server can store requested code for an application program (e.g., a JAVA applet) on a tangible non-volatile computer-readable storage medium to which it is connected. The server can retrieve the code from the medium and transmit it through network 250 to communication interface 215. The received code can be executed by processor 286 as it is received, or stored in data storage system 240 for later execution.

Data storage system 240 can include or be communicatively connected with one or more processor-accessible memories configured or otherwise adapted to store information. The memories can be, e.g., within a chassis or as parts of a distributed system. The phrase "processor-accessible memory" is intended to include any data storage device to or from which processor 286 can transfer data (using appropriate components of peripheral system 220), whether volatile or nonvolatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 240 can be a tangible non-transitory computer-readable storage medium, i.e., a non-transitory device or article of manufacture that participates in storing instructions that can be provided to processor 286 for execution.

In an example, data storage system 240 includes code memory 241, e.g., a RAM, and disk 243, e.g., a tangible computer-readable rotational storage device or medium such as a hard drive. Computer program instructions are read into code memory 241 from disk 243. Processor 286 then executes one or more sequences of the computer program instructions loaded into code memory 241, as a result performing process steps described herein. In this way, processor 286 carries out a computer implemented process. For example, steps of methods described herein, blocks of the flowchart illustrations or block diagrams herein, and combinations of those, can be implemented by computer program instructions. Code memory 241 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code ("program code") stored on a computer readable medium, e.g., a tangible non-transitory computer storage medium or a communication medium. A computer storage medium can include tangible storage units such as volatile memory, nonvolatile memory, or other persistent or auxiliary computer storage media, removable and non-removable computer storage media implemented in any method or technology for storage of information such as computer-readable instructions, data structures, program modules, or other data. A computer storage medium can be manufactured as is conventional for such articles, e.g., by pressing a CD-ROM or electronically writing data into a flash memory. In contrast to computer storage media, communication media may embody computer-readable instructions, data structures, program modules, or other data in a modulated data signal, such as a carrier wave or other transmission mechanism. As defined herein, computer storage media do not include communication media. That is, computer storage media do not include communications media consisting solely of a modulated data signal, a carrier wave, or a propagated signal, per se.

The program code includes computer program instructions that can be loaded into processor 286 (and possibly also other processors), and that, when loaded into processor 286, cause functions, acts, or operational steps of various aspects herein to be performed by processor 286 (or other processor). Computer program code (software) for carrying out operations for various aspects described herein may be written in any combination of one or more programming language(s), and can be loaded from disk 243 into code memory 241 for execution. The program code may execute, e.g., entirely on processor 286, partly on processor 286 and partly on a remote computer connected to network 250, or entirely on the remote computer.

Regarding stimulus artifact suppression, a limited CNAP conduction distance is available along the left cervical vagus nerve of rodents (e.g., ~5-15 mm of exposed nerve in a 280-300 g rat). As a result, CNAP response peaks often coincide with the stimulus artifact, necessitating the use of an artifact suppression method. It is believed that the present disclosure includes the initial disclosure of the demonstration of effective and reliable stimulus artifact suppression using cathode-first, alternating monophasic stimulation in the peripheral nervous system at conduction distances less than 1 cm.

Figure 9A:
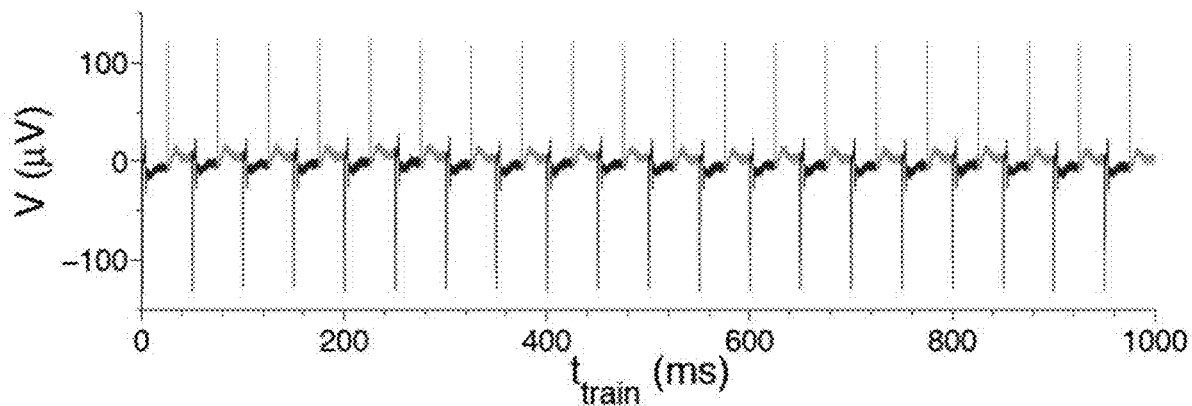
FIGS. 9A-9E show examples of evoked responses measured with various sensors, according to exemplary embodiments of the present disclosure.
Figure 9B:
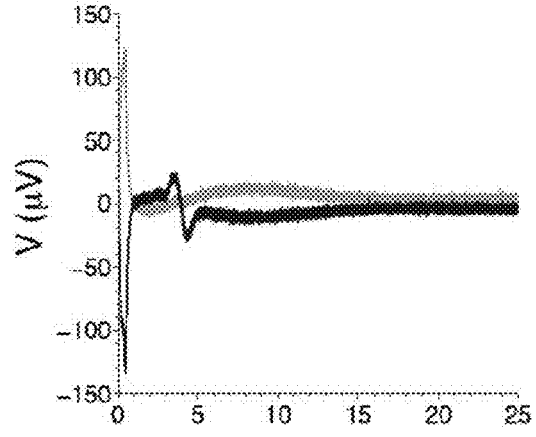
Figure 9C:
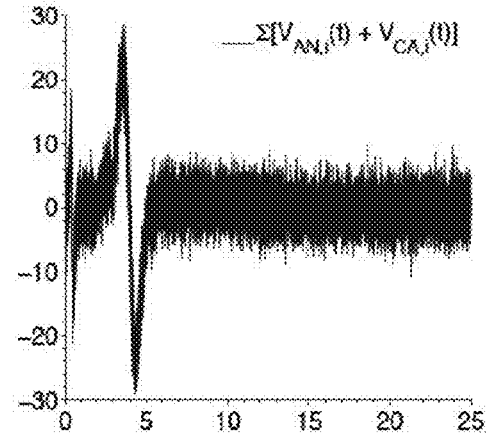
Figure 9D:
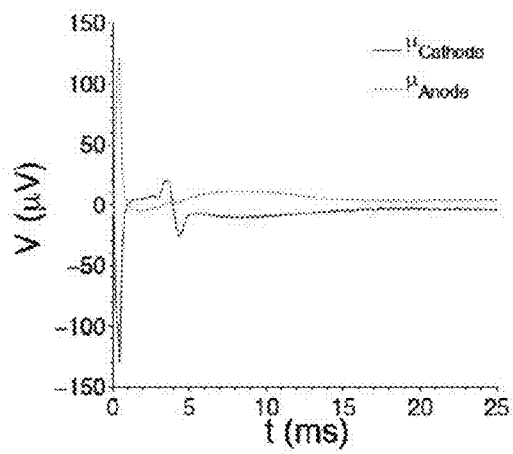

FIGS. 9A-9E summarizes the method of CNAP extraction and averaging using the measured response to a 1-s train of cathode-first, alternating monophasic stimulation ($I_{st}$=stimulus pulse amplitude=0.058 mA; $t_{st}$=stimulus pulse width=0.4 ms; PRF=pulse repetition frequency=20 Hz; $t_{train}$=stimulus train duration=1 s; Fs=sampling frequency=50 kHz; pass-band=0.001 to 10 kHz). The raw cathodal and anodal stimulus artifacts are shown in black and grey, respectively. To remove any DC offset, the average of the raw response waveform is subtracted from the recording. Then, ANC segments the raw response waveform into N periods of responses (N=PRF*$t_{train}$=20). Each period of the response waveform is then further segmented and grouped into clusters of cathodal and anodal response waveforms, respectively (FIG. 9B). The cathodal and anodal stimulus artifacts are symmetric in the recordings due to the symmetry of the anodal and cathodal phases of stimulation and the natural orientation of the recording electrodes along equipotential lines of the electric field radiating from the stimulating electrodes. The sum of each anodal and cathodal response waveform yields a cluster of artifact-free vagal nerve responses to stimulation (FIG. 9C). The mean CNAP response waveform (FIG. 9E) is the averaged cluster of CNAP responses in FIG. 1C and the sum of the mean cathodal and anodal response waveforms in FIG. 9D. A Shapiro-Wilk test for normality gives no evidence that the artifact-free stimulus responses are not normally distributed (Prob>z=0.889 when stimulating at 20 Hz for 1 s). Therefore, a response at any point in the signal is significantly different from 0 V (at $\alpha$=0.05) if the mean response and 95% CI do not cross the abscissa.

Figure 9E:
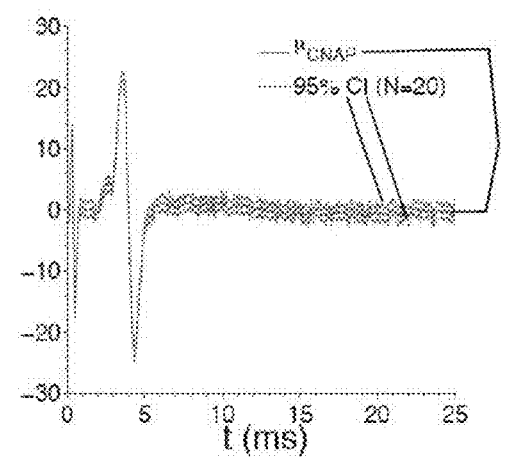

As noted above, FIGS. 9A-9E include a summary of the cathode-first, alternating-monophasic stimulation method used by ANC. ANC suppresses stimulus artifacts via a symmetric stimulation method in which the cathodal and anodal phases of stimulation have an identical shape and opposite polarity. In most cases, nerve fibers are only activated in response to the cathodal pulse (the inset overlays the stimulus waveform in red). ANC clusters each cathodal and anodal response to a train of biphasic stimuli (FIG. 9A), clusters the cathodal and anodal response waveforms (FIG. 9B), computes the artifact-free responses to each period of stimulation by summing the cathodal and anodal responses within a period of stimulation (FIG. 9C), computes the mean cathodal and anodal response waveforms (FIG. 9D), and sums the resulting waveforms to yield the mean CNAP response (E). The 95% confidence interval is shown in red in (FIG. 9E).

Figure 10A:
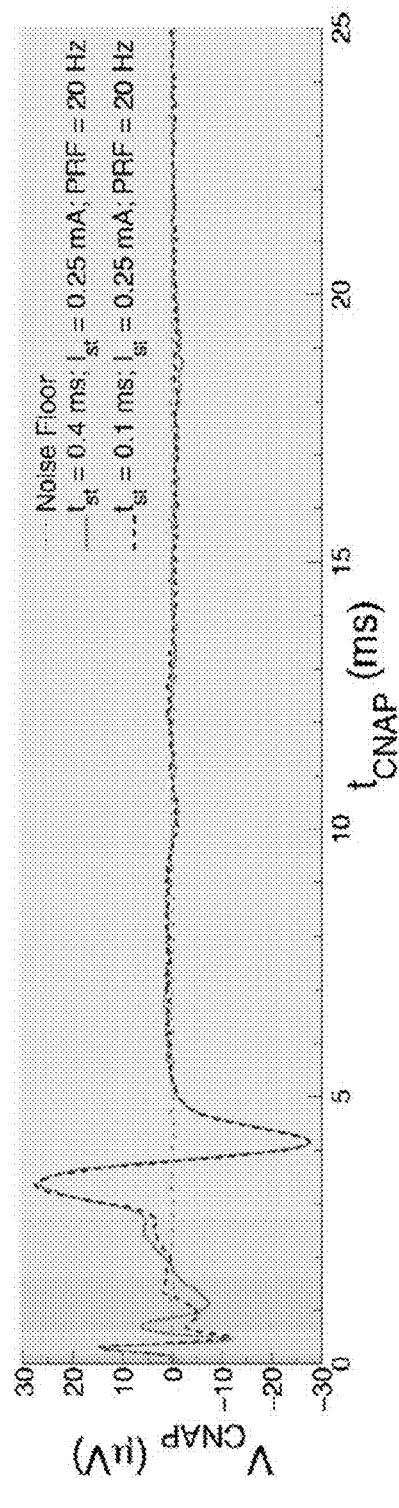
FIGS. 10A-10B show examples of classifications of evoked responses, according to exemplary embodiments of the present disclosure.
Figure 10B:
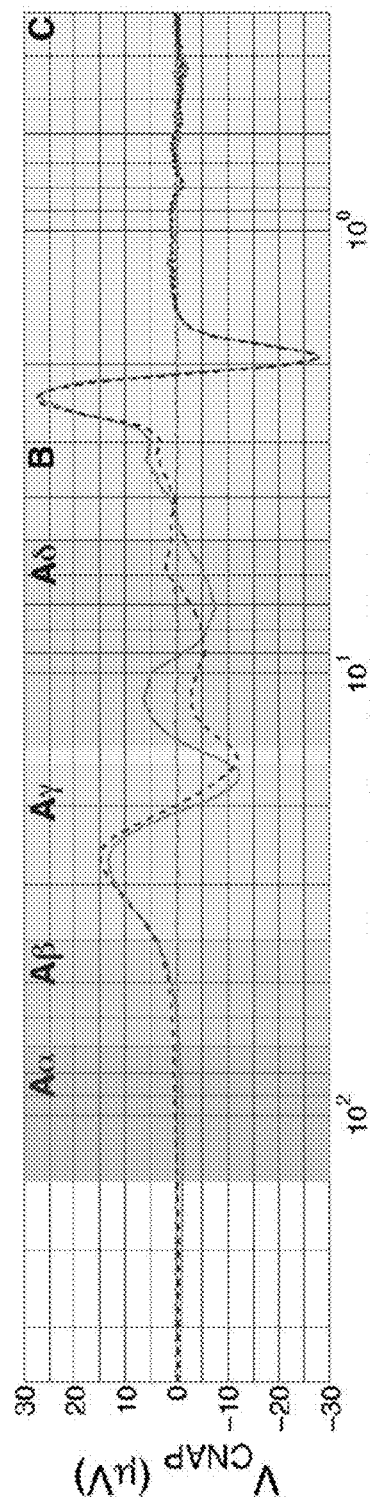

Regarding nerve response classification, ANC deconstructs the stimulus-evoked CNAP, recorded at a fixed distance from the stimulating cathode, to estimate the level and type of nerve fiber activation. Conduction velocity is used to identify distinct nerve fiber groups (i.e., neuron populations), referred to as A (fast, myelinated fibers), B (slow, myelinated fibers), or C (slow, unmyelinated fibers). FIGS. 10A and 10B describe this Letter System using data collected from the left cervical vagus nerve of a female Long-Evans rat. When recording at a fixed, known distance from the stimulating cathode, the CNAP response waveform peaks separate in time due to the differing conduction velocities of A, B and C fibers. The maximal CNAP response, otherwise referred to as maximal activation, is the CNAP response magnitude at which an increase in stimulus intensity does not produce an increase in response. By individually deriving stimulus-response relationships for A, B and C fibers, the effect of any stimulus pulse on nerve activity is directly measurable.

FIGS. 10A, 10B, and 10C can be further described as follows: An exemplary CNAP classification system (the table included in FIG. 10C) as built into ANC. FIG. 10A shows a mean CNAP response from the left cervical vagus nerve of rat. Shaded regions in FIG. 10A correspond to a conduction velocity range in FIG. 10B, which enables nerve fiber classification according to the Letter System. FIG. 10B shows a mean CNAP response from FIG. 10A plotted as a function of conduction velocity, in m/s (Conduction Distance=8.0±0.5 mm).

Regarding subjective input classification and sensory experience estimation, and using multi-contact electrodes as opposed to 1-2 channel cuff electrodes 292 (as referenced in further detail herein), stimulus-response relationships are measurable at the fascicular level, improving functional selectivity through electrode number, electrode/contact area, and spatial location relative to the fascicles/neuron populations of interest. We present an additional algorithmic approach to further optimize selectivity, using newly discovered properties of the stimulus-response relationship to automate optimal parameter selection on a subject-by-subject, task-by-task, percept-by-percept basis.

For the purpose of sensory restoration, ANC is modified to accept subjective feedback describing the quality and intensity of a perceived sensation via an iPad interface (FIG. 11) or another handheld device interface. ANC relates this information with particular stimulus parameters, sensor location, sensor input signal, and evoked afferent nerve/neuron response patterns. Using a hybrid electro-tactile haptic device (TA 2), we will determine whether this modified form of ANC is capable of reproducing complex sensory experiences via patterned electrical stimulation of cutaneous mechanoreceptors (TA 3).

As noted above, FIG. 11 shows an exemplary iPad graphical user interface (GUI) with a modified touch perception task will link the subjective experience of a sensation (i.e., the perceived spatial location, quality, and intensity of an evoked sensation relative to the expected/anticipated sensation), the measured afferent response to the stimulus that evoked the sensation, and the type of stimulus used to evoked the sensation.

Regarding stimulus-response measurement and classification, ANC measures a series of stimulus-response relationships to construct an empirical model that describes how each fiber type in any nerve of any patient will respond to any strength of electrical stimulation. This model, known as a nerve activation profile, describes the sensitivity and dynamic range of each fiber type that can be identified in a CNAP. It can be constructed in under a minute. ANC continuously updates the NAP to improve its prediction accuracy over time and adapt to the variety of factors that influence the efficacy of stimulation (e.g., circadian effects, changes in the electrode-tissue interface over time, or fiber desensitization to stimulation). New enhancements will let subjects train ANC to improve upon the user experience and to remove the need for routine full calibration cycles.

The sensitivity of each fiber group to ENS is evaluated using stimulus-response data collected at $t_{st}$=0.4, 0.2 and 0.1 ms. If necessary, the operator may define all stimulus and recording parameters (default parameters: stimulus type=constant current; stimulus waveform=cathode-first, alternating monophasic stimulation; PRF=20 Hz; $t_{train}$=1 s; Fs=50 kHz; pass-band=0.001 to 10 kHz). Starting with $t_{st}$=0.4 ms, ANC incrementally increases the stimulus amplitude, stimulates the nerve, and records that resulting CNAP response. Between trials, the mean CNAP response is computed, the peak fiber responses are located and classified, and the data are stored in local memory. Following Trial 1, the response magnitude from the target fiber group is always compared to that from the previous trial. When stimulus intensity is increased and the target fiber response magnitude no longer increases (i.e., if a fiber group is maximally activated), ANC stores the stimulus parameters and responses from the previous trial. Next, ANC decreases the stimulus amplitude according to (1) until parameters that yield a predefined percentage of maximal activation are located (e.g., 25% maximal activation, defined as a target fiber response having a magnitude that is 25% of its maximal response magnitude). The same process is repeated using $t_{st}$=0.2 and 0.1 ms, respectively. An error tolerance of 5% is initially used to classify all fiber response magnitudes to account for the effects of noise.

$$Q_n = Q_{n-1}\left(1 + \frac{V_\odot - V_{CNAP,n-1}}{k \cdot V_\odot}\right) \quad (1)$$

In (1), $Q_{n-1}$ is the stimulus charge per phase from the most recent trial (in C/Ph), $V_\odot$ is the target fiber response voltage (in V), $V_{CNAP,n-1}$ is the fiber response voltage from the most recent trial, and k is a scaling factor that modulates the magnitude of the stimulus intensity adjustment (e.g., when k is greater than unity, it reduces the intensity of the stimulus charge adjustment; when k is less than unity, it amplifies the intensity of the stimulus charge adjustment). The new stimulus pulse amplitude is calculated by dividing the new stimulus charge per phase, $Q_n$, by the pulse duration used in the preceding trial (i.e., $I_{st,n}=Q_n/t_{st,n-1}$).

Results indicated a rapid loss of C-fiber activation with constant stimulation. For example, FIGS. 12A-12D shows an example of how a nerve adapts to a constant electrical stimulus in a relatively short time ($I_{st}$=0.2 mA; $t_{st}$=0.5 ms; PRF=20 Hz; $t_{train}$=30 s). Linear regression was performed in STATA 12 to test for a statistically significant order effect, a characteristic feature of SIDNE. A regression model slope coefficient that is significantly different from 0 suggests a relationship/change among the CNAP features of interest (i.e., $A\gamma^+$, $B^+$, or $C^+$) and stimulus number (i.e., the sequential number assigned to each cathodal stimulus pulse within the 30-s train of stimuli delivered at 20 Hz). Significance tests of the slope coefficients suggest that, with an increasing number of stimuli, Aγ fiber excitability increases (p-value=$4.82E^{-9}$) and C fiber excitability decreases (p-value=$5.34E^{-74}$). A change in stimulus-driven nerve activation suggests an analogous change in the evoked sensation relative to the sensation expected by the subject.

Figure 12A:
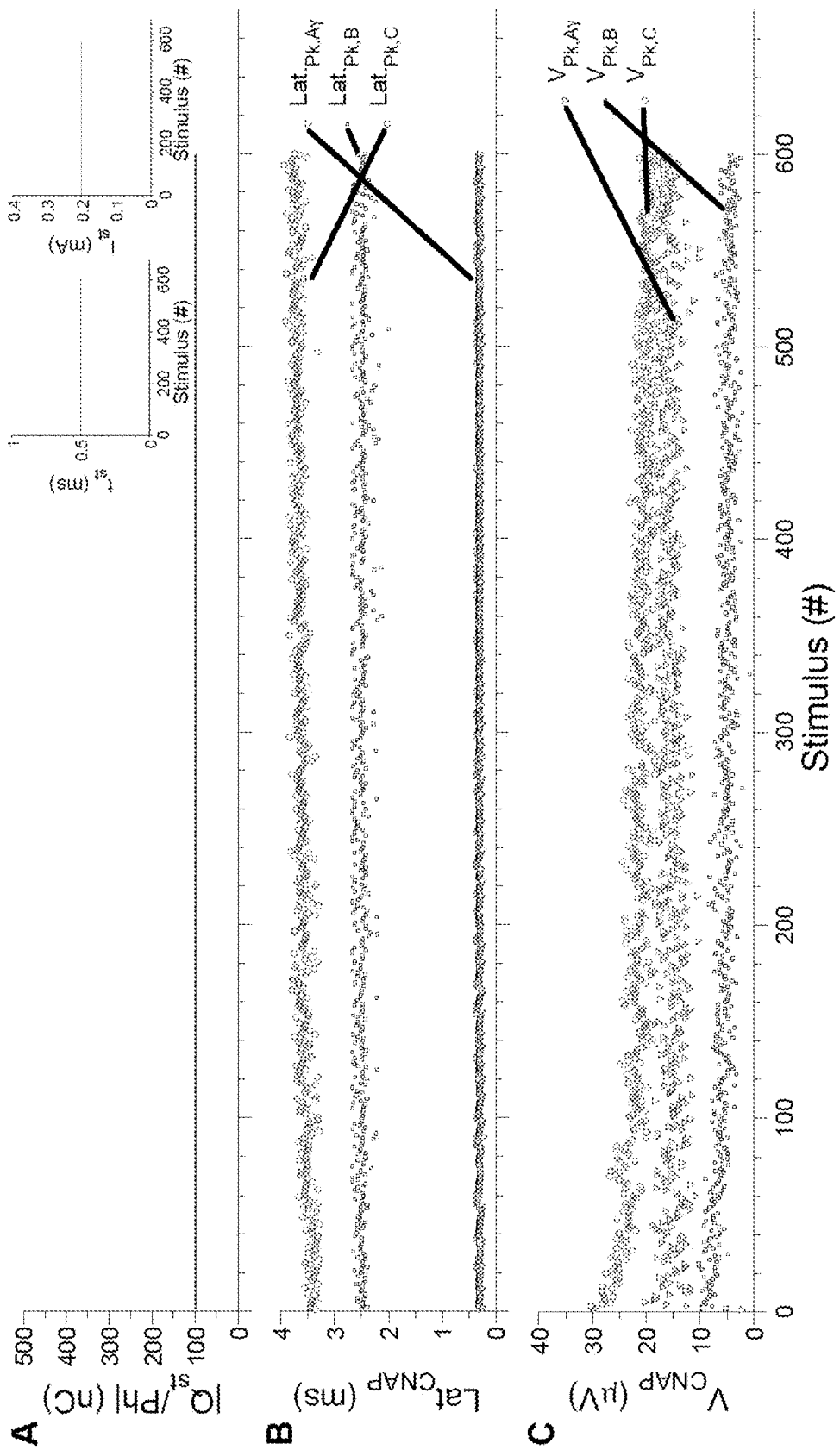
FIGS. 12A-12D show examples of updating an evoked response database useful for a pattern classifier, according to exemplary embodiments of the present disclosure.
Figure 12B:
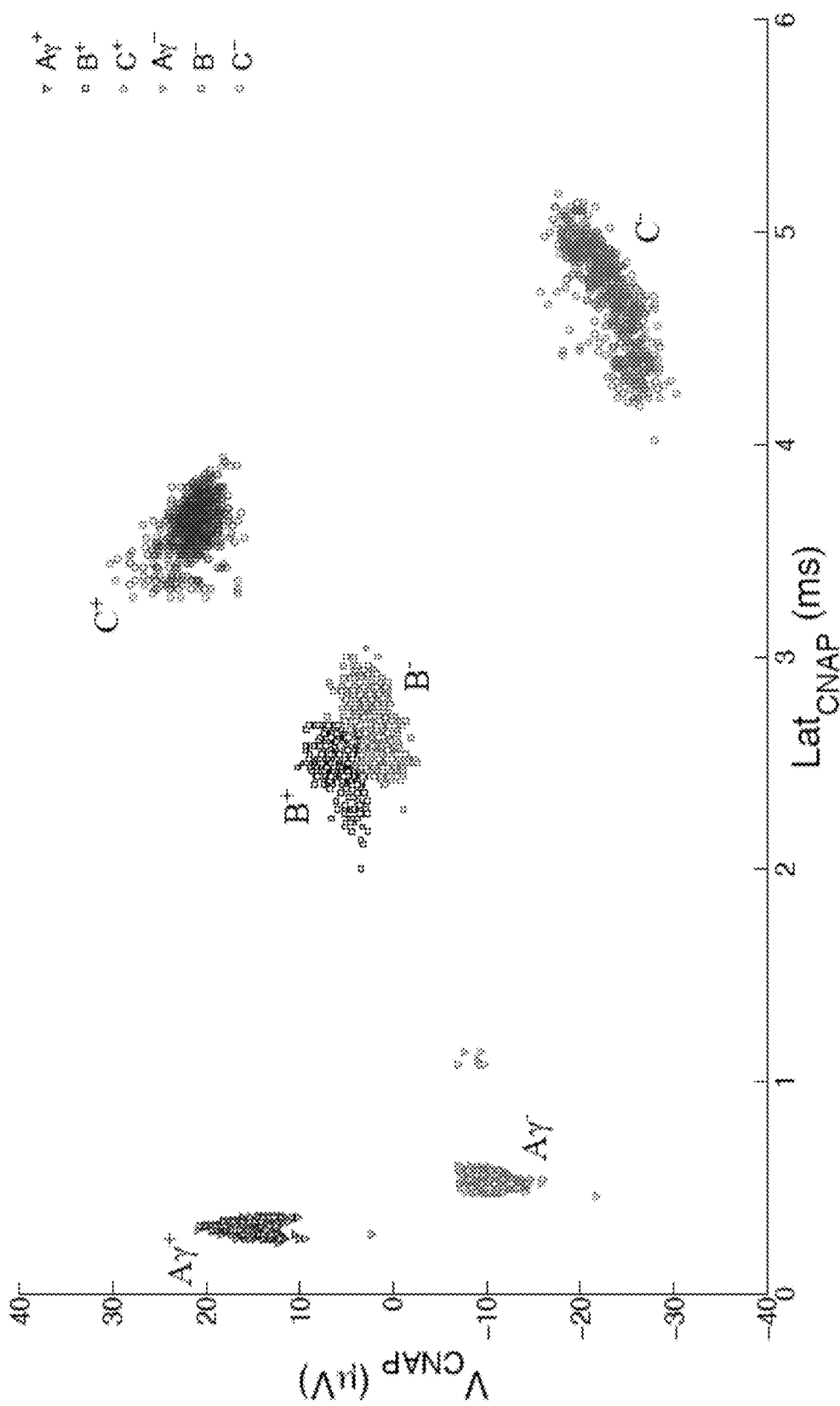
Figure 12C:
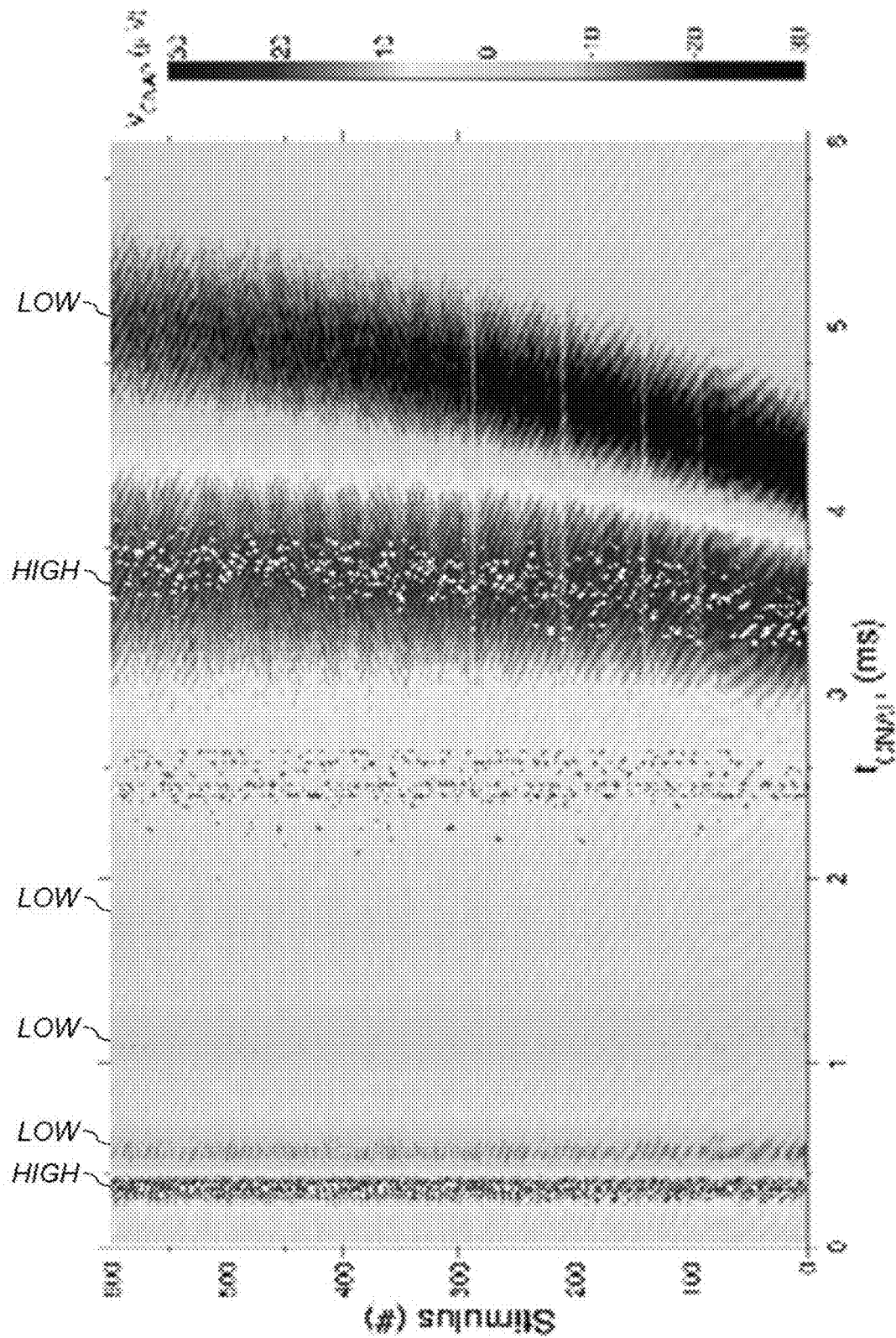
Figure 12D:
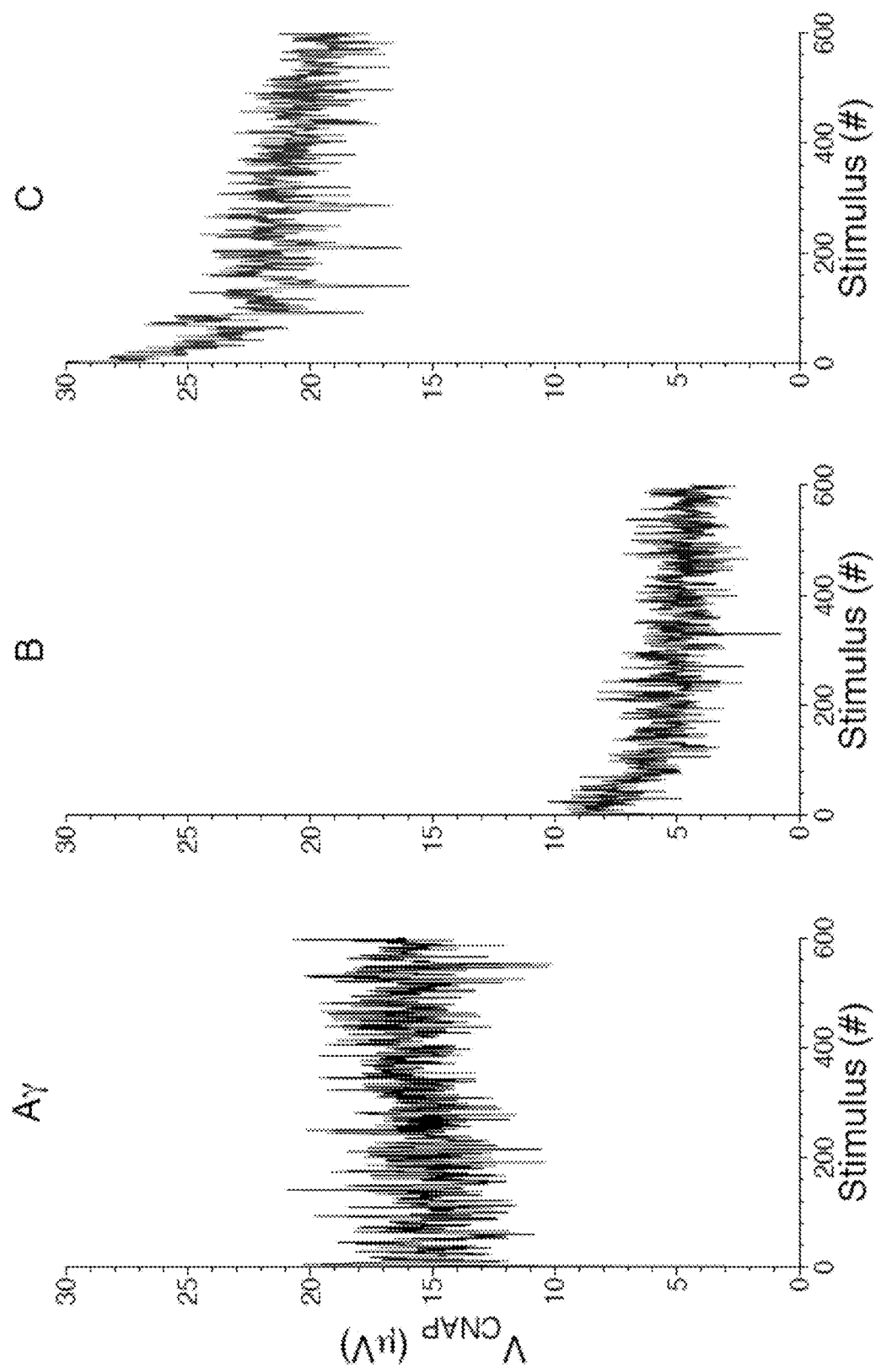

FIGS. 12A-12D can be further described as follows. Subsection A of FIG. 12A shows a constant stimulus charge of 100 nC/Ph was applied at 20 Hz for 30 s. The insets show the pulse duration and amplitude of each stimulus ($I_{st}$=0.2 mA; $t_{st}$=0.5 ms). Subsection B of FIG. 12A shows a measured Aγ, B and C peak response latencies relative to stimulus onset (ms). Subsection C of FIG. 12A shows a measured Aγ, B and C fiber peak response amplitudes relative to baseline (μV). FIG. 12B shows a clustered stimulus response data from B-C. Amplitude and latency values associated with the second deflection of the diphasic fiber responses are also plotted in grey. FIG. 12C shows a color map representation of all stimulus response data shown in A-C ($N_{CNAP}$=600 CNAP responses). Stimulus onset occurs at the intersection of the Stimulus # and $t_{CNAP}$ axes. Note the significant increase in C peak latency and decrease in response voltage as Stimulus # increases. FIG. 12D shows a fiber peak voltage as a function of stimulus number. Aγ fibers become slightly more excitable, as inferred from a general increase in the peak amplitude over the 600 stimuli. B and C fibers show significantly less activation as stimulus number increases.

Figure 13A:
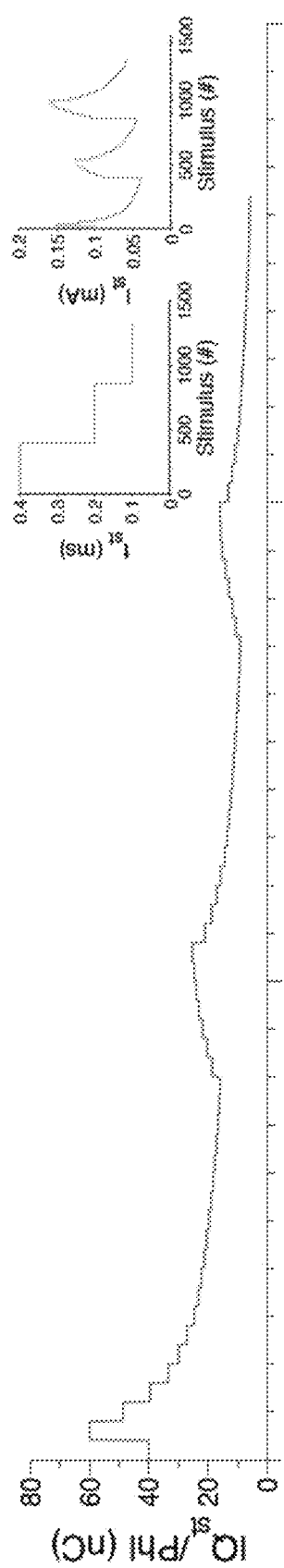
FIGS. 13A-13F show examples of updating a nerve activation profile (NAP), according to exemplary embodiments of the present disclosure.
Figure 13B:
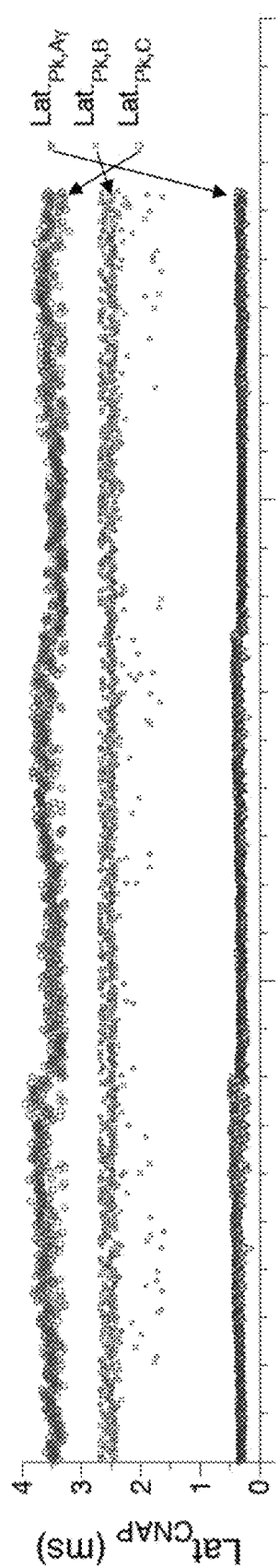
Figure 13C:
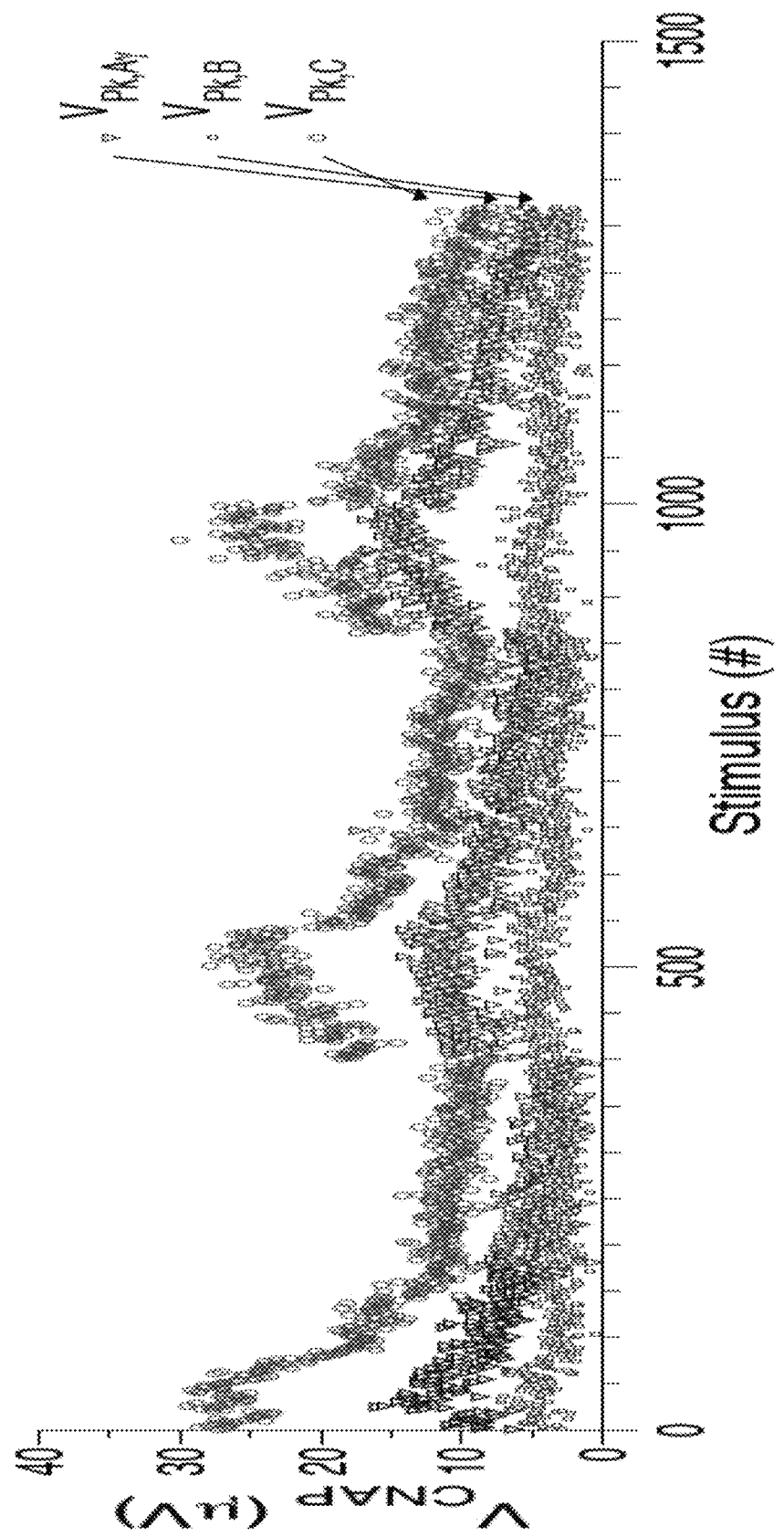
Figure 13D:
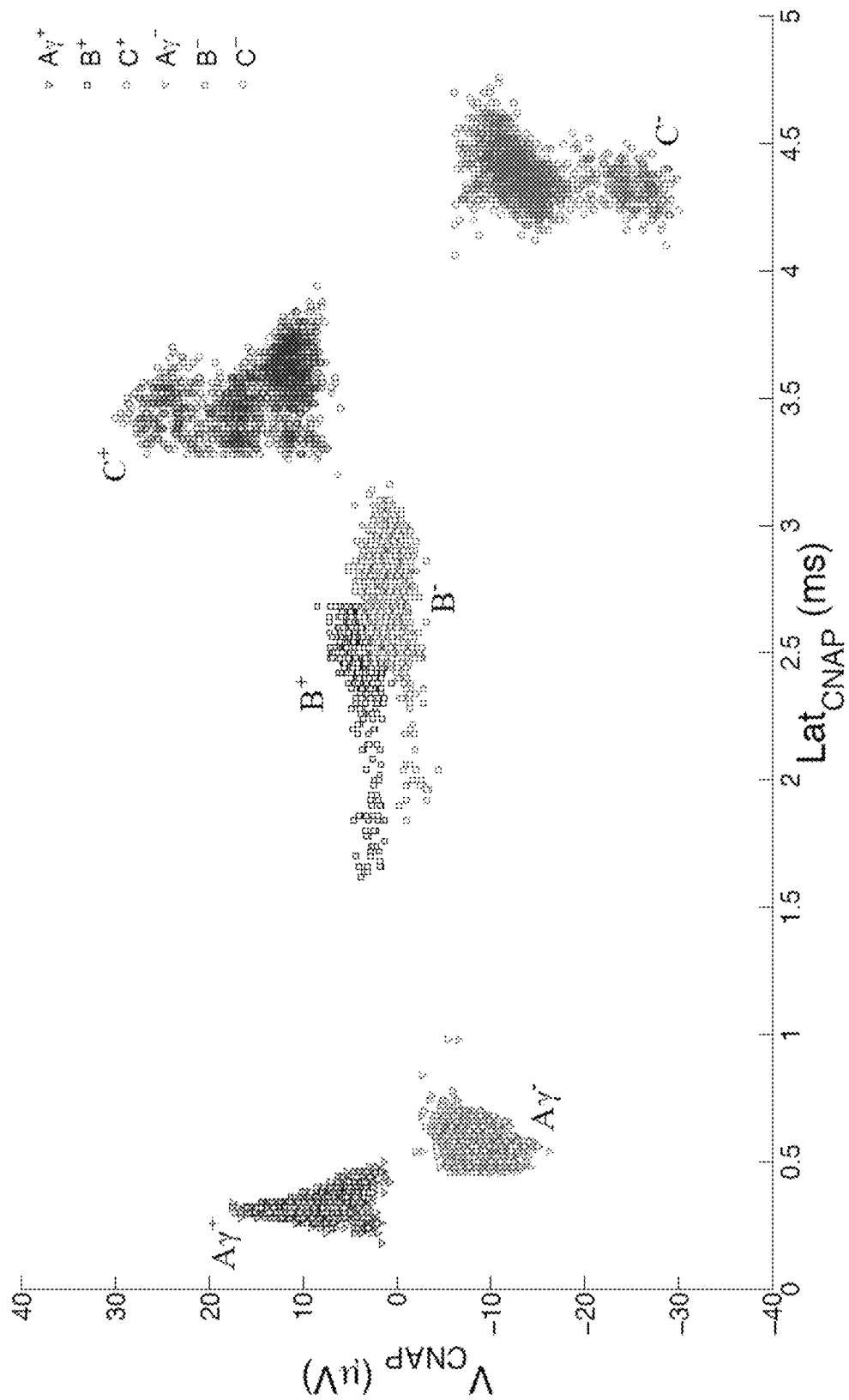
Figure 13E:
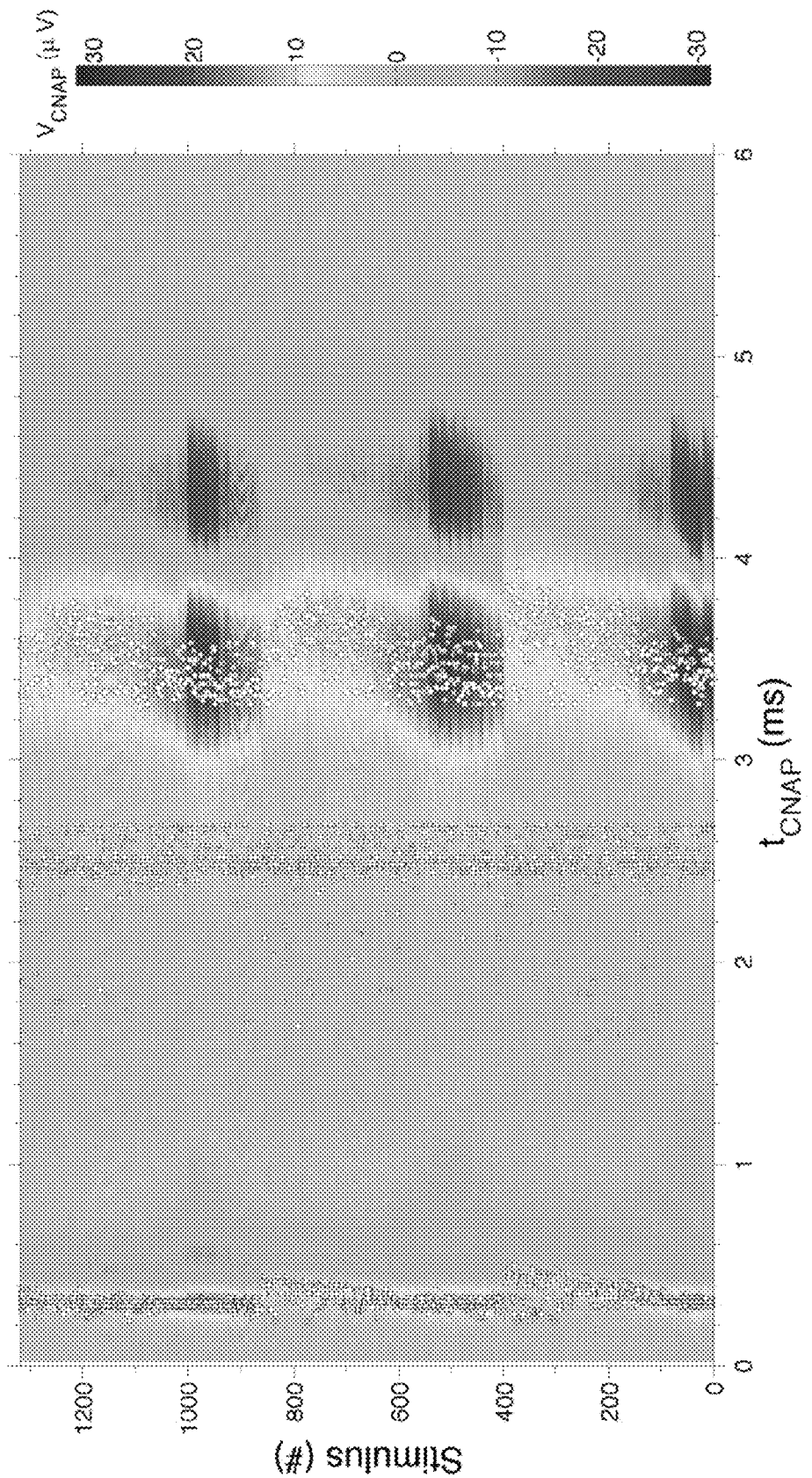

Regarding autonomous stimulus-response measurement and classification, FIGS. 13A-13F summarize a set of stimulus-response data that ANC collected from C fibers in the left cervical vagus nerve of the same rat whose data is represented in at least FIGS. 12A-12D (PRF=20 Hz; $t_{train}$=1 s; Conduction Distance=8 mm; $N_{CNAP}$=66 trials×20 CNAP responses/trial=1320 CNAP responses). FIGS. 13A-13C show all 1320 Aγ, B, and C fiber CNAP response latencies and voltages ($N_{parameter}$=20 responses per stimulus parameter combination; $N_{combo}$=66 unique parameter combinations). Although Aγ and B fiber stimulus-response data is collected, all stimulus intensity adjustments are based on the magnitude of the mean C fiber response in relation to the maximal response voltage. In FIG. 13D, data from FIGS. 13A-13C is clustered by response voltage and latency. Local minima from each fiber group are also plotted to demonstrate that other features of the CNAP response, such as peak-to-peak voltage and area, can be measured and used by ANC. A color map of all 1320 CNAP responses is shown in FIG. 13E (voltage is represented as a color according to the scale to the right of the figure). Finally, the mean CNAP responses are plotted by trial in FIG. 13F. Mean peak latencies are computed from the latencies of each individual stimulus response shown in FIGS. 13A-13E.

Figure 13F:
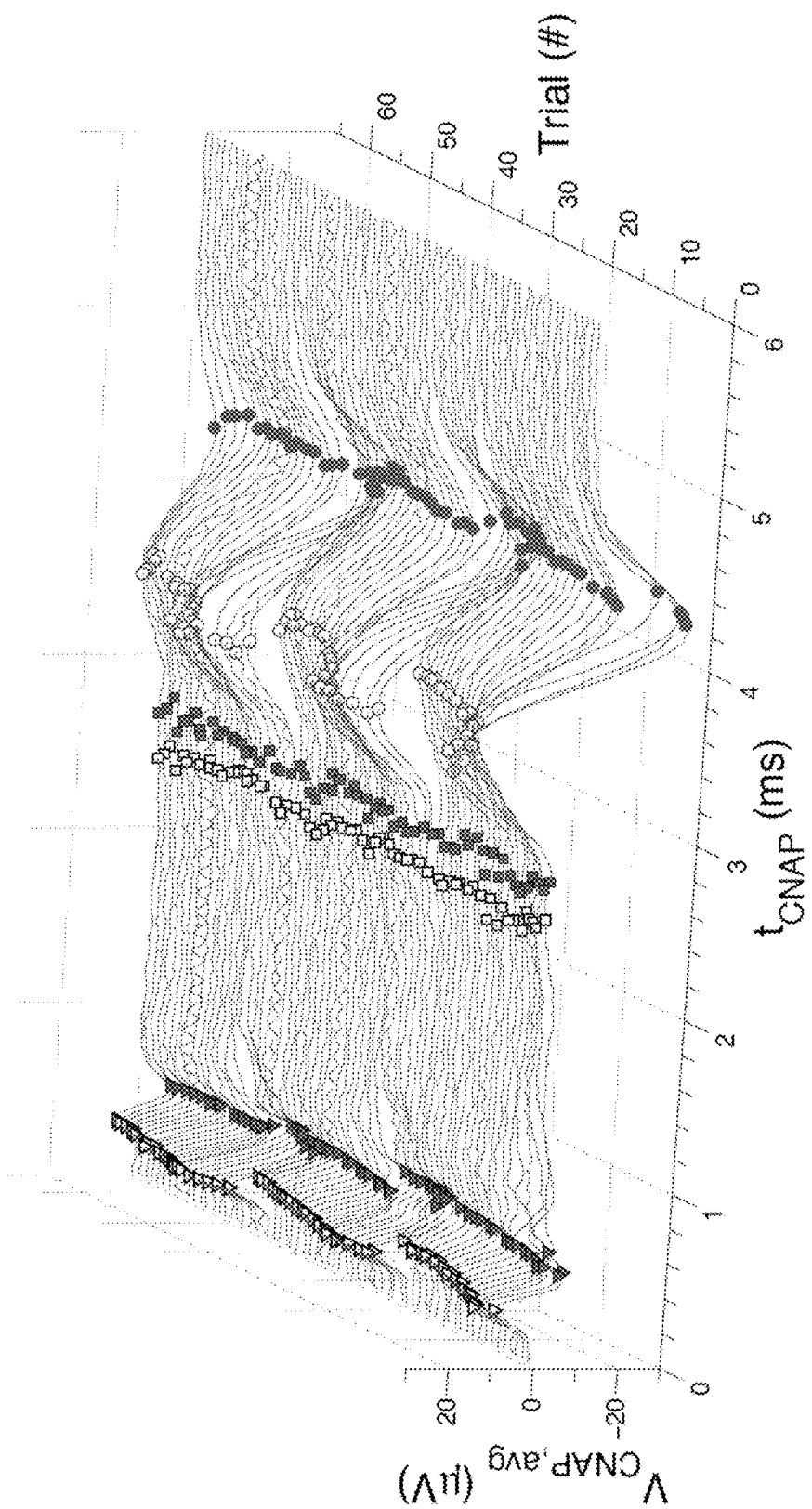

FIGS. 13A-13F can be further described as follows, identifying autonomously collected stimulus-response data from the left cervical vagus nerve of a female Long-Evans rat. FIG. 13A shows a stimulus charge per phase, in nC/Ph, for the entire vagal C-fiber activation profile-mapping period (ANC constructs a unique activation profile for each stimulated nerve and neuron type; the activation profile serves as a guide when maintaining or adjusting nerve activation for an experimental or therapeutic purpose). The insets show the pulse duration and amplitude of each stimulus. FIG. 13B shows measured Aγ, B and C peak response latencies relative to stimulus onset (ms). Latency increases with decreasing stimulus intensity for Aγ and C fibers, but not for B fibers. FIG. 13C shows measured Aγ, B and C fiber peak response amplitudes relative to baseline (μV). FIG. 13D shows clustered stimulus response data from B-C. Amplitude and latency values associated with the second deflection of the diphasic fiber responses are also plotted in grey. FIG. 13E shows a color map representation of all stimulus response data shown in A-C ($N_{CNAP}$=66 trials×20 CNAP responses/trial=1320 CNAP responses). Stimulus onset occurs at the intersection of the Stimulus # and $t_{CNAP}$ axes. FIG. 13F shows a mean CNAP response computed from data collected during each trial of stimulation ($N_{CNAP, avg}$=20 CNAP responses/trial). Stimulus onset is at the intersection of the $V_{CNAP, avg}$ and $t_{CNAP}$ axes.

Regarding the slope-activation relationship, ANC rapidly identifies the parameter space for each fiber group in a nerve in the form of an activation profile. An activation profile is autonomously constructed for each fiber type using measured stimulus-response data and a newly discovered mathematical formula that relates threshold current (i.e., rheobase current) to fiber activation level. A set of activation profiles for each fiber group in a nerve constitutes a nerve activation profile.

The key to constructing a NAP is in a newly discovered, predictable relationship between the rheobase current, $I_{Rh}$, and its corresponding fiber activation level, λ ($I_{Rh}$ is the slope of a charge-duration (CD) line described by the Weiss equation). When all possible CD lines are constructed from a set of stimulus-response data, each will represent a unique activation level, λ. If the slope of each line (i.e., $I_{Rh}$) is plotted against its corresponding activation level, λ, an exponential slope-activation relationship is observed. It is unique to each subject, nerve and neuron type, and allows ANC to adapt to changes at the device-tissue interface over the course of an experiment or therapy. To our knowledge, this is the first discovery and documentation of the relationship.

To derive the slope-activation relationship for vagal Aγ, B and C fibers, ANC first sorts the stimulus-response data in ascending order by the evoked response voltage. Each fiber response voltage is then normalized with respect to the maximal recorded response voltage and converted to a percentage of maximal activation. The largest observed response voltage represents maximal activation. All associated stimulus parameters are stored along with the measured nerve responses (In Phase I, ANC will be enhanced to accept subjective feedback from the user and sensor input from the sensorized prosthesis. ANC will be further enhanced with at least 40 neural recording channels and 40 neural stimulation channels.).

Next, ANC clusters the evoked fiber responses and associated stimulus parameters by activation level (a 5% error tolerance is used by default). Within each cluster, the data is sorted by pulse duration (i.e., $t_{st}$). If multiple entries have the same pulse duration and evoke the same level of activation, they are replaced with an average of the duplicate entries. ANC then searches for clusters with at least 2 pulse durations represented. Using these data, ANC computes the best-fit CD lines using least-squares linear regression.

The slope of each computed CD line (i.e., $I_{Rh}$) is plotted against the associated percent maximal fiber activation, λ. To model the slope-activation relationships, ANC first computes the natural logarithm of each slope. Then, the best linear fit to the natural logarithm-transformed data is computed using least-squares linear regression. The resulting equation has the form $\hat{I}_{Rh}=ar^\lambda$, where $\lambda=V_{trial}/V_{max} \cdot 100$ is the percent maximal activation, a is the predicted slope of the CD line for 0% maximal activation, and r is a constant that determines the rate at which the slope of a CD line increases as activation level increases. In linear form, the slope-activation equation is $\ln(\hat{I}_{Rh})=\lambda \ln(r)+\ln(a)$. If M=ln(r) and B=ln(a), then $\hat{I}_{Rh}=e^{M\lambda+B}$, where M is the slope, B is the y-intercept (i.e., the threshold current for 0% maximal activation), and λ is the percent maximal activation. This can be used in place of $I_{Rh}$ within the Weiss equation. In doing so, an equation that can be used to predict how a target fiber group will respond to any strength of ENS is created (2). The Weiss equation is shown above (2) for reference.

$$Weiss: \frac{1}{t_{st}} \int_0^{t_{st}} I_{st} dT = \frac{I_{Rh}(t_{st}+\tau_{SD})}{t_{st}} = \bar{I}_{st} \quad (2)$$

$$NAP: \frac{1}{t_{st}} \int_0^{t_{st}} I_{st} dT = \frac{e^{M\lambda+B}(t_{st}+\tau_{SD})}{t_{st}} = \bar{I}_{st}$$

Figures 5A, 5B:
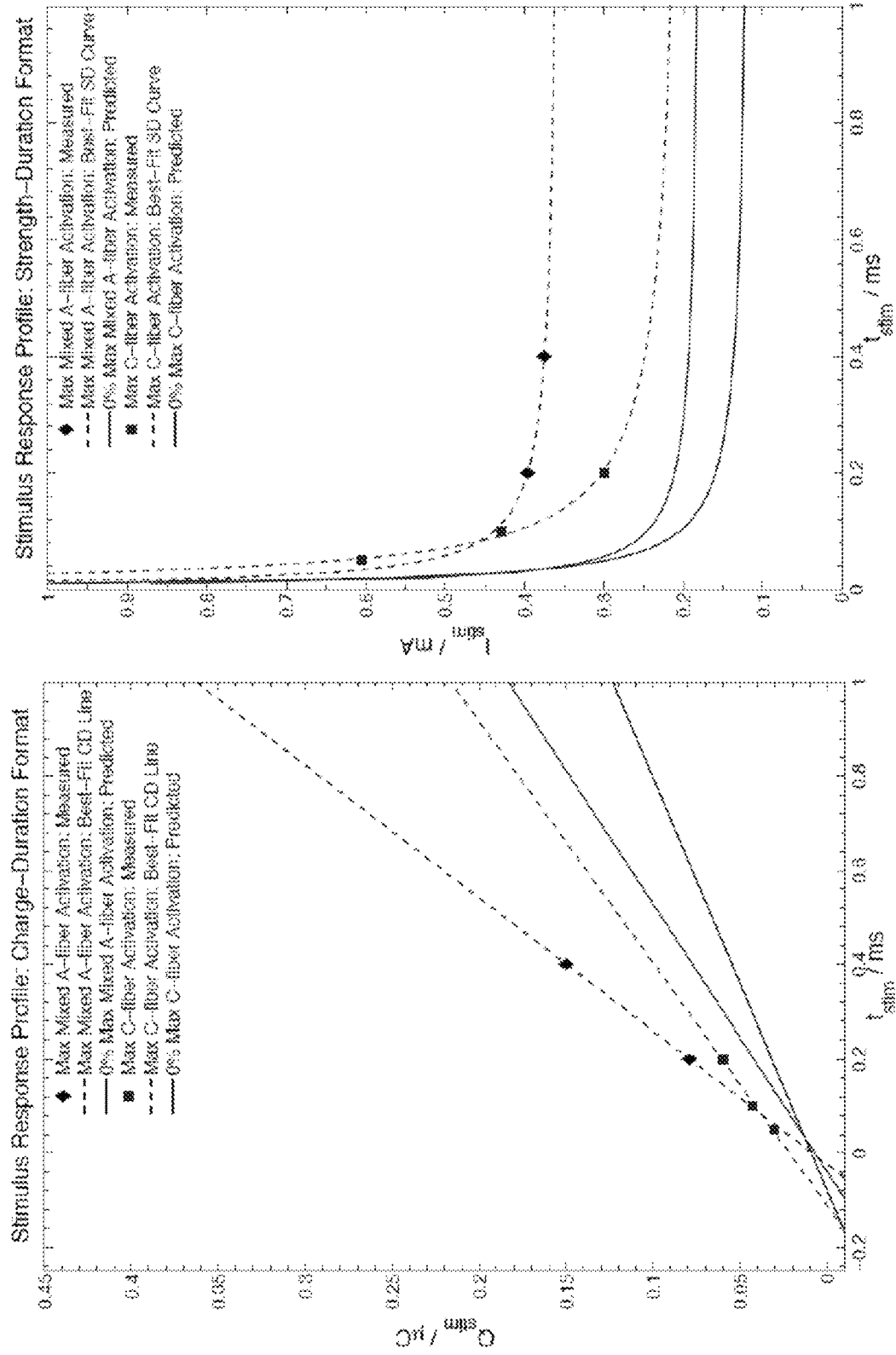
FIGS. 5A-5B show experimental data and predicted data, according to exemplary embodiments of the present disclosure.
Figure 6:
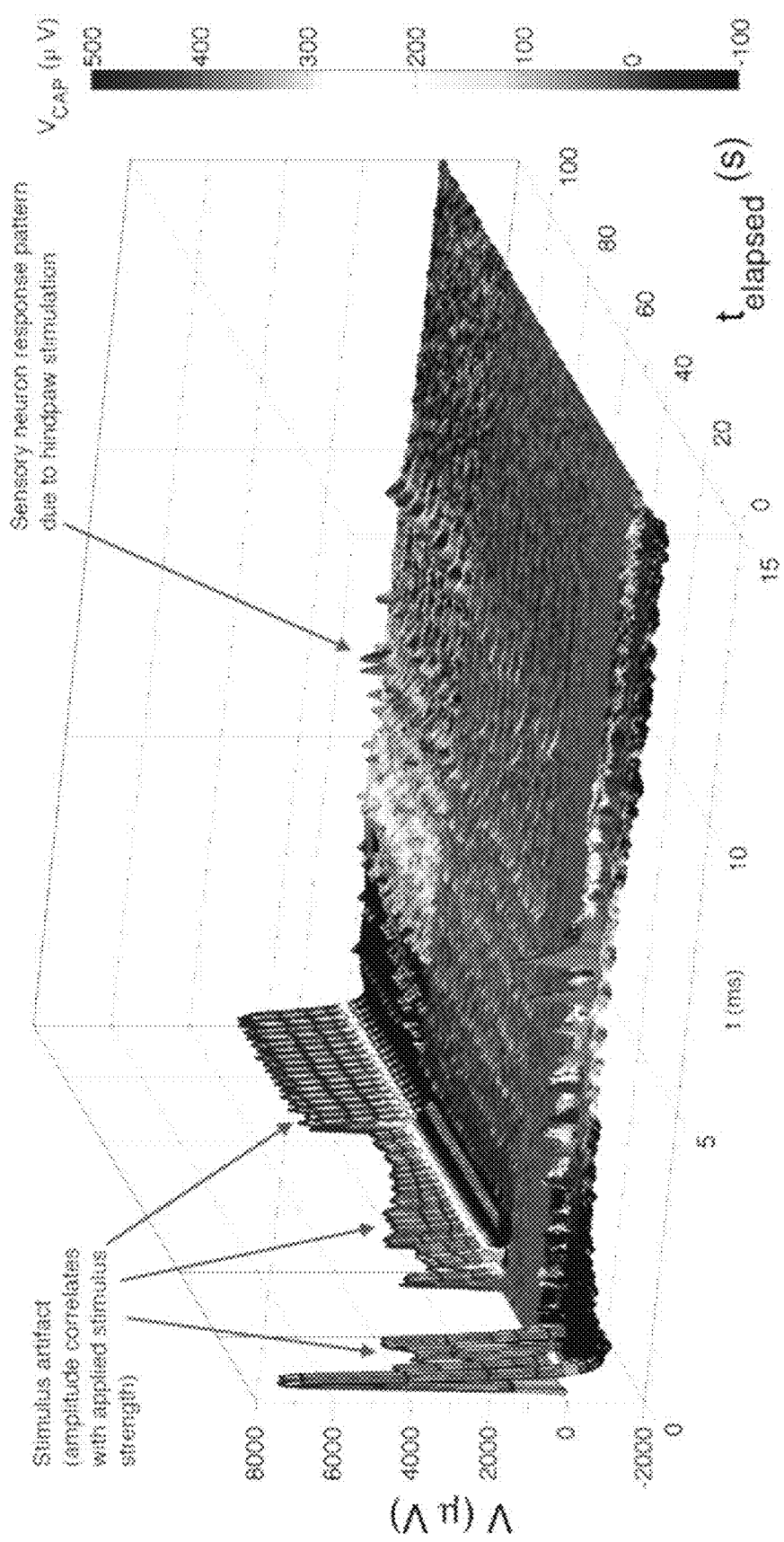
FIG. 6 shows experimental data of neuron response to hindpaw stimulation, according to an exemplary embodiment of the present disclosure.
Figure 7:
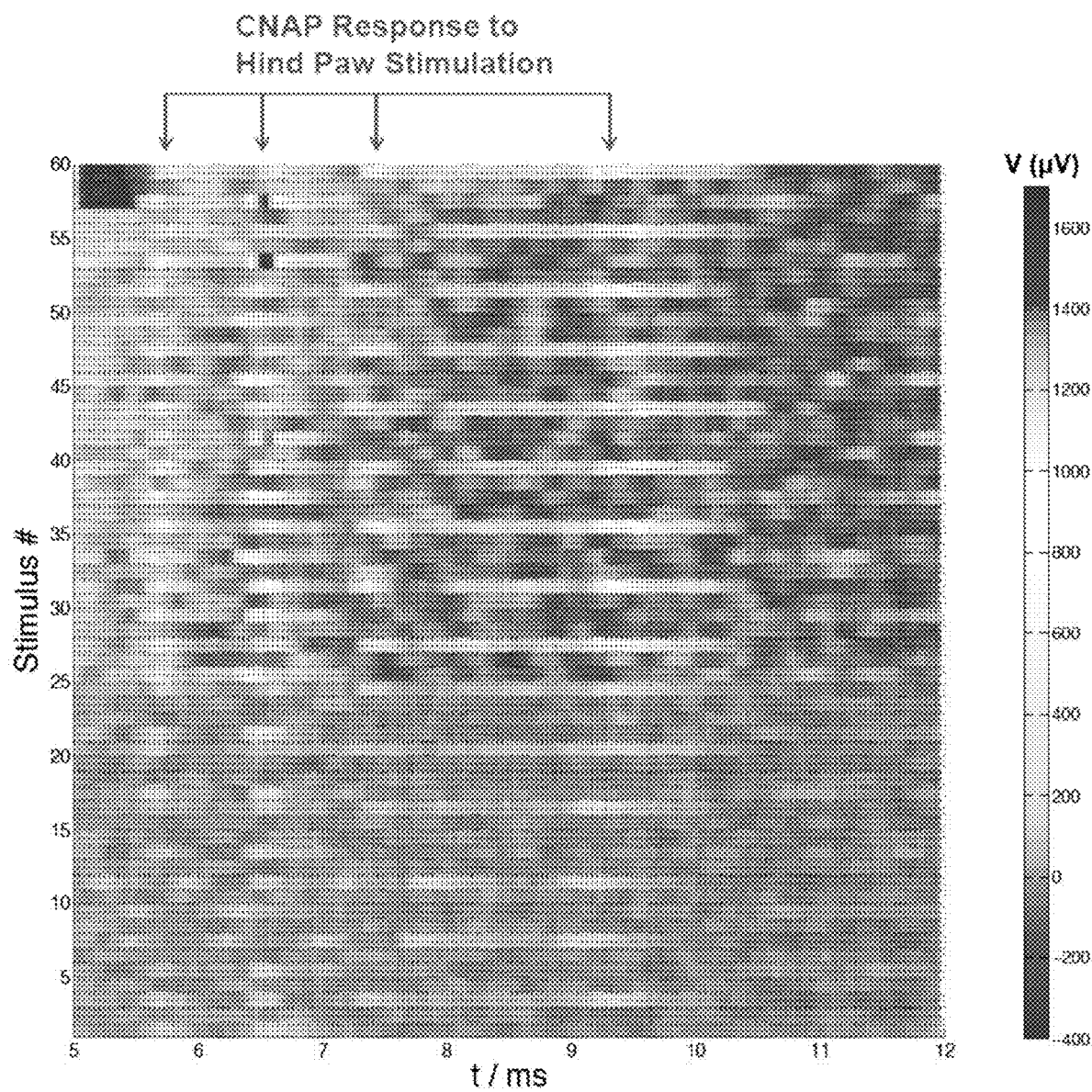
FIG. 7 shows exemplary experimental data of neuron response to hindpaw stimulation of the present dislcosure. The CNAP recording location was the left sciatic nerve. The stimulus location was the left hind paw (pad). The stimulus type was constant-current, cathode-first, alternating monophasic stimulation. Qst/phase increases with stimulus number. Each trace is a CNAP response to a single stimulus. Stimulus intensity is increased every 4th stimulus.
Figure 14A:
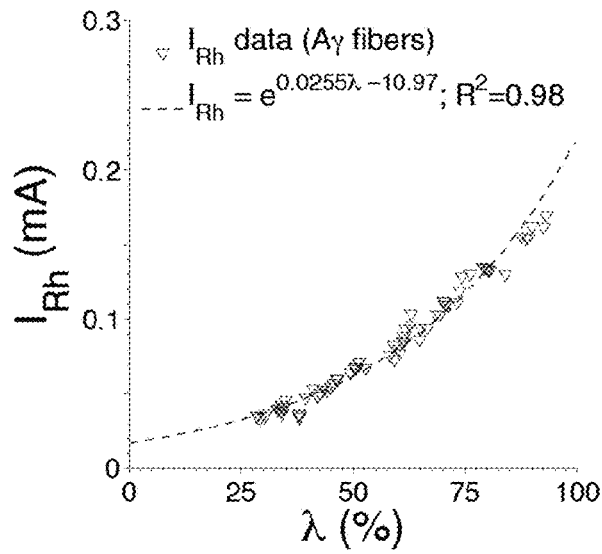
FIGS. 14A-14E show examples of nerve response to an electrical stimulus, according to exemplary embodiments of the present disclosure.
Figure 14B:
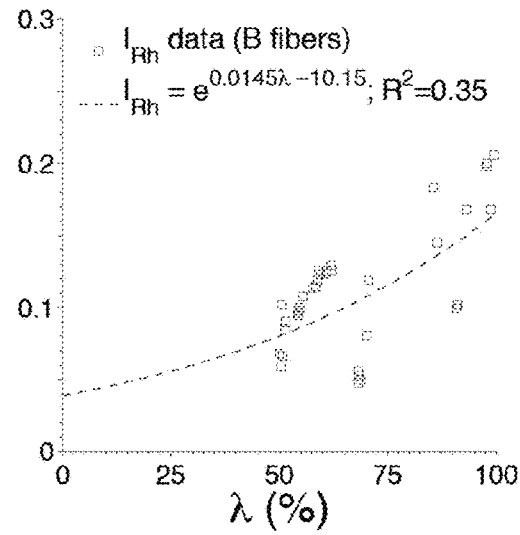
Figure 14C:
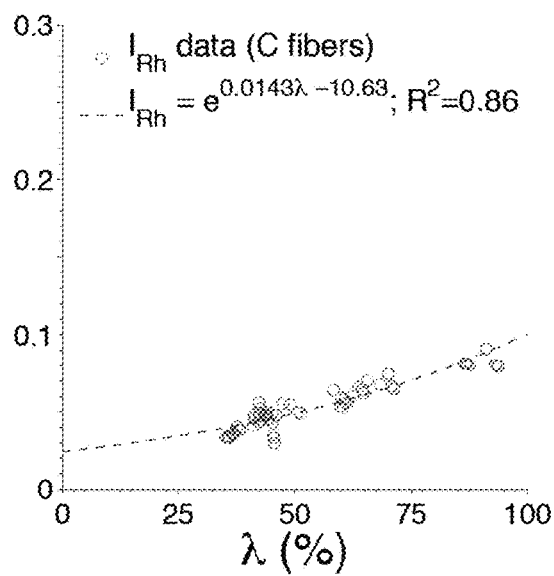

FIGS. 14A-14C show the slope-activation data along with the associated equations and goodness-of-fit metrics for vagal Aγ, B and C fibers (derived using stimulus response data from at least FIGS. 5A and 5B). The slope-activation data for Aγ fibers is least variable ($R^2$=0.98), followed by C ($R^2$=0.86) and then B fibers ($R^2$=0.36). A consistently poor signal-to-noise ratio is likely to blame for the poor fit to B fiber slope-activation data. A poor fit to the slope-activation data will translate to larger predictive errors once the activation maintenance mode of ANC is initiated. The model will evolve as ANC collects more data, however. Erroneous or inaccurate values in the slope-activation relationship are replaced once ANC locates the stimulus parameters that yield precisely the desired response. In connection with the foregoing, FIG. 5A shows a stimulus-response profile of mixed A and C fiber types in the left sciatic nerve of Rat TMR6, with data presented in charge-duration line format. FIG. 5B shows a stimulus-response profile of mixed A and C fiber types in the left sciatic nerve of Rat TMR6, with data presented in strength-duration curve format.

Figure 14D:
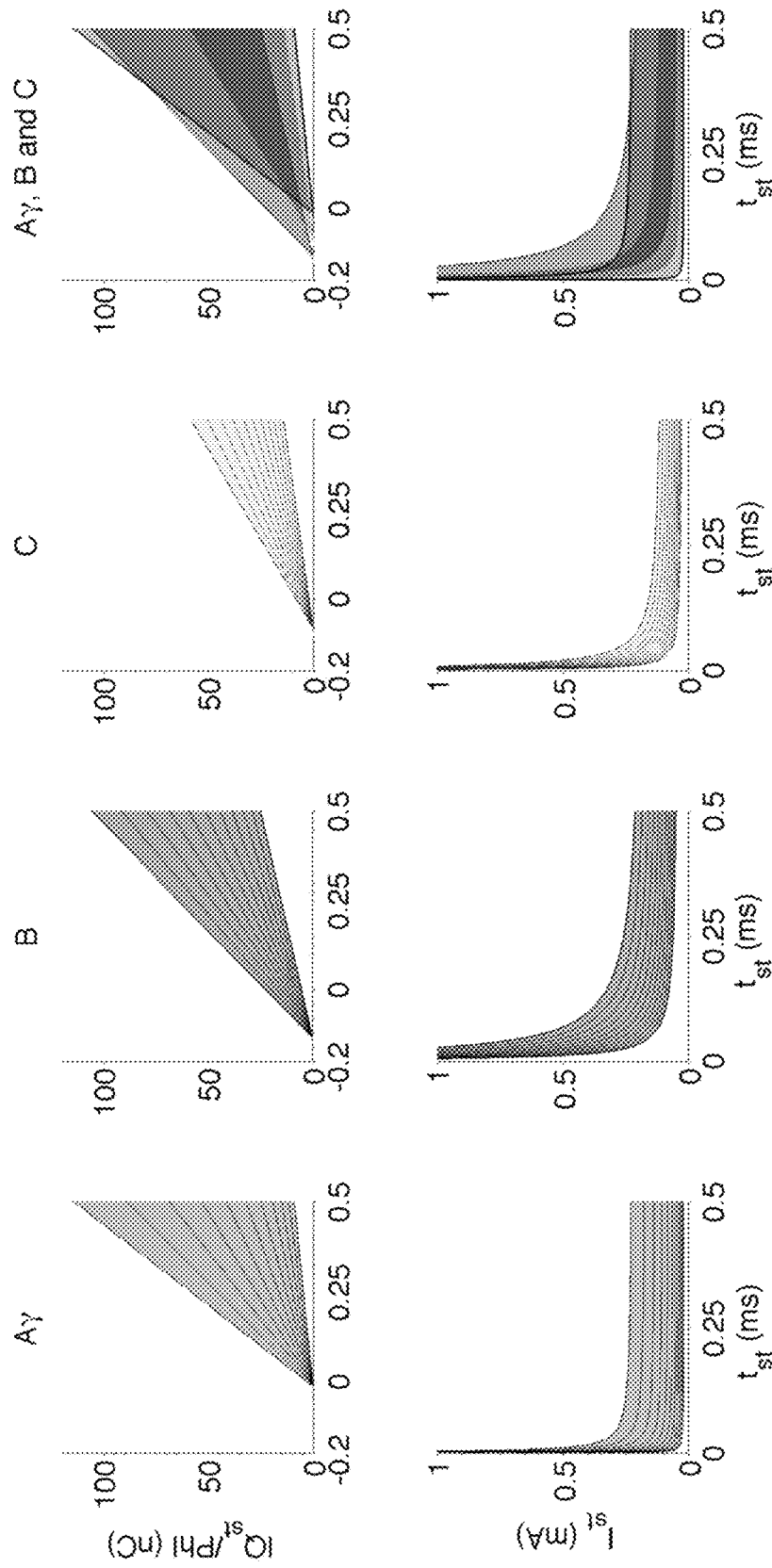
Figure 14E:
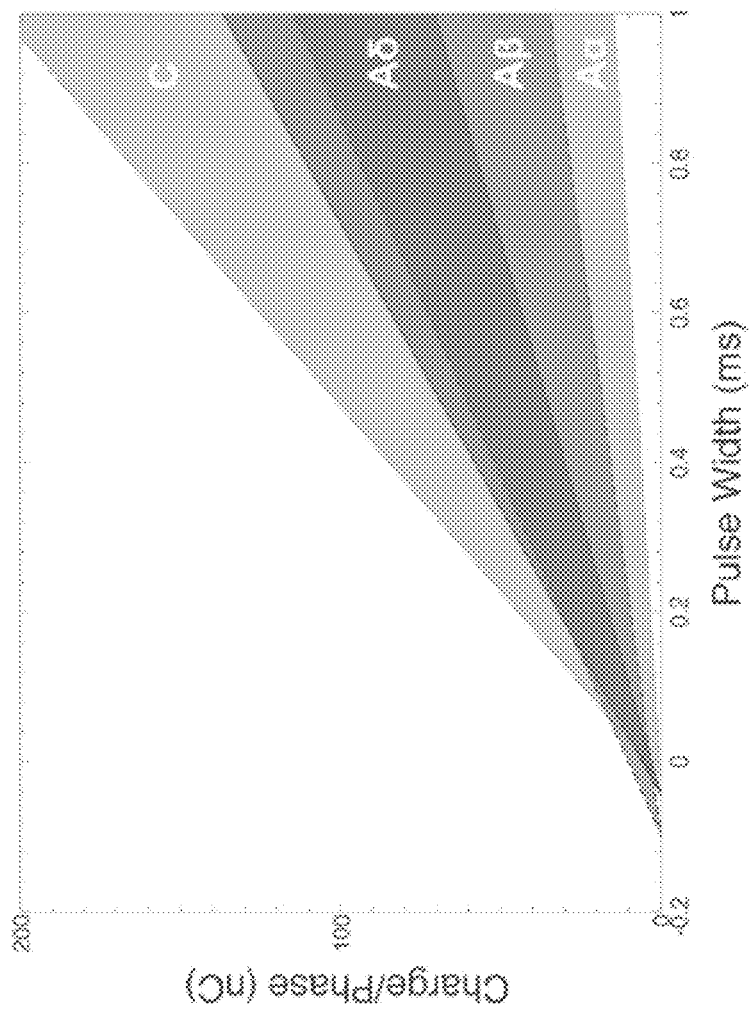

FIGS. 14A-14D can be further described as follows. FIGS. 14A-14C show slope-activation data for Aγ (FIG. 14A), B (FIG. 14B) and C fibers (FIG. 14C) for a single animal. For each fiber group, the rheobase current, $I_{Rh}$, is plotted against its corresponding level of maximal activation, λ. Data shows an exponential increase in rheobase current for a linear increase in percent maximal activation. Best-fit curves are calculated for each fiber type through a least-squares linear regression of the natural logarithm-transformed slope-activation data. The coefficients M and B of the slope-activation equation are placed in the generalized form of the Weiss equation, producing a single equation that predicts how the target fiber type will response to any strength of stimulation. The goodness-of-fit is best for Aγ fibers ($R^2$=0.98), followed by C and B fibers ($R^2$=0.86 and 0.35, respectively). A poor fit is most closely associated with a poor signal-to-noise ratio. FIG. 14D shows activation profiles for Aγ (left), B (middle-left) and C (middle-right) fibers with predicted CD lines (top row) and SD curves (bottom row) for 0 to 100% maximal activation, in 10% increments. The right column shows the NAP, which predicts how all Aγ, B and C fibers in the nerve will respond to any strength of stimulation.

Regarding the nerve activation profile, the activation profile for each fiber type is formed from the slope-activation equation and an estimate of the SD time constant, $\tau_{SD}$. The absolute value of the mean of the x-intercept values from the CD lines is used as an estimate of $\tau_{SD}$. Given the subject, nerve, and fiber-specific constants M, B, and $\tau_{SD}$, (2) predicts the population response of any nerve fiber group to any strength of constant-current stimulation. This unique attribute is especially evident when solved for λ in (3).

$$\lambda = \frac{1}{M}\left[\ln\left(\frac{I_{st} \cdot t_{st}}{t_{st} + \tau_{SD}}\right) - B\right] \quad (3)$$

FIG. 14D graphically depicts the activation profiles that ANC constructed for vagal Aγ, B and C fibers using (2). The activation profile can be expressed in CD (top row) or SD form (bottom row). When the activation profile from each fiber group is overlaid, the NAP is complete. The NAP in FIG. 14D describes how the left cervical vagus nerve of one particular rat will respond to any strength of electrical stimulation. To aid interpretation, predicted CD lines (top row) and SD curves (bottom row) are shown within the parameter space for [0, 10, 20, . . . , 100]% maximal activation. Note the nonlinear increase in slope with a linear increase in percent maximal activation, a property described by the coefficient M in the slope-activation equation. In Phase I, ANC will be modified with the ability to create independent activation profiles for each recording channel, fascicle, fiber population, mechanoreceptor, nociceptor, and/or thermoceptor. Subjective feedback, from the touch perception task (TPT), will be associated with each activation profile.

ENS holds the potential to modulate or control the function of almost every tissue in the body. Control is established by artificially modulating the firing activity of existing neural pathways with patterned electrical impulses from an implantable or external device. To maximize control over an application requiring sensory restoration via a multi-channel peripheral nerve interface, the correct strength and pattern of ENS is applied to selectively activate and control one or more specific neural pathways linked to specific types of cutaneous sensory receptors whose combined activation encodes the foundation of sensation. Establishing control with conventional stimulation paradigms is problematic, however, as the degree of neural activation in response to a given dose of stimulus varies greatly from patient to patient (e.g., due to genetic differences, the tissue/immune response to the implant, or environmental factors) and changes over time in individual patients.

ANC is a form of artificial intelligence that adjusts stimulus parameters in real time so that control is maintained over one or more neural pathways that mediate the target therapeutic effect and the off target effects (i.e., side effects). With the closed-loop, biofeedback-driven control provided by ANC, the degree of nerve fiber activation, ranging from 0 to 100%, is controlled in the same manner across patients and within the same patient over time. ANC serves as a tool to advance our understanding of the relationships between the degree and pattern of neural activation and therapeutic efficacy. Moreover, it allows for the rapid if not immediate deployment of stimulus parameters that are optimized for each patient, nerve and neuron type. It is a new alternative to the long, burdensome device tuning system that is currently in use that can pave the way for a new standard of care.

In at least one technical approach described herein, the present disclosure includes disclosure of a developed scalable, high-resolution and self-optimizing haptic and electro-tactile display to provide naturalistic sensory feedback to TSR patients through software-guided, patterned electrical, mechanical, and thermal stimulation of sensory receptors that are accessible through the re-innervated skin surface. Hybrid transducers, each comprising an electrode, solenoid, heating element, and cooling element, will be controlled with ANC software according to decoded afferent (sensory) response patterns, sensorized prosthesis output, skin temperature and impedance, contact force, and subjective feedback from the user describing the sensory and emotional quality and intensity of an evoked sensation. This novel approach to sensory restoration employs multiple degrees of freedom and learning algorithms to enable personalized sensory experiences that more closely resemble patient needs and expectations. Table 1 summarizes the sensory receptors targeted with this display. Table 1 shows select properties of mechanoreceptors, nociceptors, thermoceptors and proprioceptors:

TABLE 1

Select properties of mechanoreceptors, nociceptors, thermoceptors and proprioceptors

| Receptor | Subtype | Mode of stimulation | Percept | Fiber type | LTA/HT* | RA/SA** |
|---|---|---|---|---|---|---|
| Mechanoreceptor | Meissner corpuscle | Dynamic deformation | Stroking, fluttering, slip | Aβ | LT | RA |
| | Pacinian corpuscle | Vibration | Vibration, grasp, pressure | Aβ | LT | RA |
| | Merkel cell-neurite complex | Indentation depth | Shape, texture, fine tactile discrimination | Aβ | LT | SA |

TABLE 1-continued

Select properties of mechanoreceptors, nociceptors, thermoceptors and proprioceptors

| Receptor | Subtype | Mode of stimulation | Percept | Fiber type | LTA/HT* | RA/SA** |
|---|---|---|---|---|---|---|
| | Ruffini corpuscle | Stretch | Stretch, direction, hand position, finger position (proprioception) | Aβ | LT | SA |
| | Free nerve endings (C fiber LTM) | Touch | Pleasant touch, social interaction | C | LT | SA |
| | G-hair | Light touch | Skin movement | Aβ | LT | RA |
| | D-hair | Light touch | Skin movement | Aδ | LT | RA |
| | Field | Stretch | Skin stretch (proprioception) | Aα, Aβ | LT | |
| Nociceptor | Mechano-nociceptor | Blunt trauma | Skin injury, pain | Aδ, C | HT | SA |
| | Thermal-mechanical | Intense heat | Burning pain | Aδ | HT | SA |
| | Thermal-mechanical | Intense cold | Freezing pain | C | HT | SA |
| | Polymodal nociceptor | Trauma | Skin injury, burning pain | Aδ, C | HT | SA |
| Thermoceptor | Cool | Cold (25° C.) | Cool | Aδ | LT | SA |
| | Cold | Intense cold (<5° C.) | Cold | C | LT | SA |
| | Warm | Warm (41° C.) | Warm | C | LT | SA |
| | Heat | Hot (>45° C.) | Hot | Aδ | LT | SA |
| Proprioceptor | Muscle spindle primary | Muscle length/ velocity | Muscle movement | Aα | LT | SA |
| | Muscle spindle secondary | Muscle stretch | Muscle stretch | Aδ | LT | SA |
| | Golgi tendon organ | Muscle contraction | Muscle contraction | Aα | LT | SA |
| | Joint capsule/ kinesthetic | Flexion/ extension | Joint angle, joint motion | Aβ | LT | SA |

*Low threshold/high threshold
**Rapidly adapting/slowly adapting

The design of the exemplary tactile transducers 295 (also referred to as actuators 104 or elements containing actuators 104) referenced herein is a novel design of a compact tactile device which integrates mechanical, electrical and thermal stimulations for finger tips aiming at integration with a kinesthetic feedback system. The transducer array is an mxn array of electromechanical actuators with thermal excitations and sensors.

The scheme of the tactile transducer 295 with a single actuator 104 is presented in FIG. 17. As referenced herein, a transducer 295 may include an actuator 104 and other elements referenced in FIG. 17, for example, and the terms transducer 295 and actuator 104 may be used interchangeably in certain respects. As shown in FIG. 17, an exemplary actuator 104 of the present disclosure comprises a solenoid of conducting wire 300 (also referred to herein as an electromagnetic coil 300, in some embodiments) that is coupled to an armature 302 and a movable plunger 304. Both the armature 302 and the plunger 304 are made of soft iron in at least one actuator 104 embodiments. Solenoids 300 convert electrical current flowing through the coil into a linear mechanical force that produces the displacement of the plunger, as identified in the two arrows with the "Magnetic Force" reference in FIG. 17. When current flows through the solenoid 300, it creates a magnetic attraction force between the armature 302 and the plunger 304 and, thereby, reduces the air gap distance between them. The amount of force generated depends on the amplitude of current, number of turns in the coil 300 and the geometry and position of the armature 302 and plunger 304. The design shown in FIG. 17 is adopted for reduced variability of the force with the displacement of the plunger 304. The magnetic force is always attractive irrespective of the direction of the current. To obtain a bidirectional displacement of the plunger 304, an elastic spring 306 is employed which opposes the magnetic force, as indicated by the bidirectional arrow with the "Spring Force" reference in FIG. 17. A thin aluminum brush 308 is used in between the coil 300 and the plunger 304 to allow smooth sliding of the plunger 304. One or more miniature pressure sensors 310 is/are attached to one end of the spring 306 to measure the pressure on the plunger 304. As shown in FIG. 17, and in at least one embodiment, an exemplary actuator 104 can be at or about 15 mm high, have a width dimension (including the plunger 304, coil 300, and armature 302, as shown in FIG. 17) of at or about 8 mm, and have a width dimension of 10 mm when also including the cooling element(s) 314 and heating element(s) 316, referenced in further detail below.

The input of the transducer 295 is a rectangular pulse train generated from a microcontroller and the output is the motion of the plunger 304, such as by way of the tip 305 of plunger 304 contacting the user's skin, which creates fingertip stimulation, as indicated by the arrow with the "Fingertip Force" reference in FIG. 17. The intensity and the frequency of the mechanical stimulation depend on the amplitude and the frequency of the pulse train. The pressure sensor 310, in at least one embodiment, takes a direct current (DC) voltage and outputs a variable DC voltage according to the pressure change.

Electrical stimulations are provided to the fingertip through the movable plunger 304. A flexible conductive wire 300, as noted above, is attached with the plunger 304 which carries the electrical stimulations.

On the top hard surface 312 of the transducer 295 (or actuator 104), there will be two Peltier elements; one for cooling (one or more cooling elements 314) and one for heating (one or more heating elements 316). These two elements 314, 316 provide thermal stimulation. A Peltier cooler (an exemplary cooling element 314) or a Peltier heater (an exemplary heating element 316) is a solid-state active heat pump which transfers heat from one side of the device (actuator 104/transducer 295) to the other, with consumption of electrical energy. It can be used either for heating or for cooling. This device is useful when it is necessary to transfer heat from one medium to another on a small scale. They are about 1 mm$^2$ in surface area in at least one embodiment. The temperature difference it creates depends on the amplitude of the input DC current. With an input current of 0.5 A, for example, a temperature difference of 72K is available.

FIG. 18 presents the top view of a 4×4 tactile transducer 295/actuator 104 array 400. The signal paths for the independent control of each transducer 295 are routed between every row and column via signal paths 402. A technique of addressing each transducer 295/actuator 104 can be similar to the strategy for controlling the pixels in a LCD display via active matrix addressing, for example. The signal path 402 also contains various excitation inputs and sensor outputs, in various embodiments. Arrays 400 can include four actuators 104 (such as an a 2×2 grid), nine actuators 104 (such as in a 3×3 grid), sixteen actuators 104 (such as in a 4×4 grid, as shown in FIG. 18), or more or fewer actuators 104, as may be desired. In at least one embodiment, array 400 comprises sixteen actuators 400 in a 4×4 grid, with length and width dimensions of at or approximately 50 mm.

The technology referenced herein solves challenges faced by previous attempts at designing realistic, usable haptic and electro-tactile displays, namely a lack of day-to-day reproducibility, an inability to reproduce realistic multi-component sensory stimuli in users of the device(s), and an inability to scale the technology. FIG. 17 shows a cross-section of an exemplary hybrid electro-tactile haptic display element with temperature, pressure, and impedance sensing inputs and thermal, mechanical, and electrical outputs. FIG. 18 shows a top view of a 16-element array. Specialized software will relate afferent nerve response patterns to subjective assessments of a sensation. Along with temperature, pressure, and impedance information, the software will learn user preference so that the display output matches user expectations.

Others in the field are focused primarily on haptic technology, which uses grids of vibrating elements to induce a sensation in a user. Those working with electro-tactile technology focus primarily on improved circuitry (e.g., high-speed switching networks and new electrode or stimulation topologies), improved selectivity (e.g., mechanoreceptor activation in isolation versus in combination, achievable only through intensive, time-consuming parameter search processes), and improved day-to-day usability (i.e., approaches that do not require intensive calibration on a day-to-day or hour-to-hour basis, such as accounting for changes in skin impedance with additional support circuitry).

The technology disclosed herein differs from existing solutions and approaches in several ways:

(A) It provides a truly personalized interface that improves its performance on a day-to-day basis (i.e., it does not require re-calibration on a day-to-day basis). For example, continuous response monitoring is provided from an implanted, multi-channel electrode array, coupled with an adaptive controller that adjusts output parameters to evoke a particular pattern of neural responses associated with a discrete or complex sensations, overcomes the performance limitations imposed upon existing technology due to changes in skin impedance and differing orientations of the electro-tactile or haptic interface relative to the original calibration position (B) The framework/platform supports external or implantable haptic, electro-tactile, or combination haptic/electro-tactile interfaces (C) The technology is scalable (in terms of cost, the type and intensity of a sensation, and the resolution of a sensation)

(D) The technology has the capacity to predict a sensation that a user might experience using a particular combination of stimulus parameters using relationships between a physiological response, such as a nerve signal, the parameters of stimulation, and the subjective input from a user (E) The technology bridges the gap between a subjective experience of a sensation and the hardware/software that evokes the sensation (i.e., it has the capacity to learn patterns of stimulation/output that induce a very specific sensation in a user, sensations that can only be understood as real by the user due to previous experiences of the sensation in a natural manner).

Figure 19:
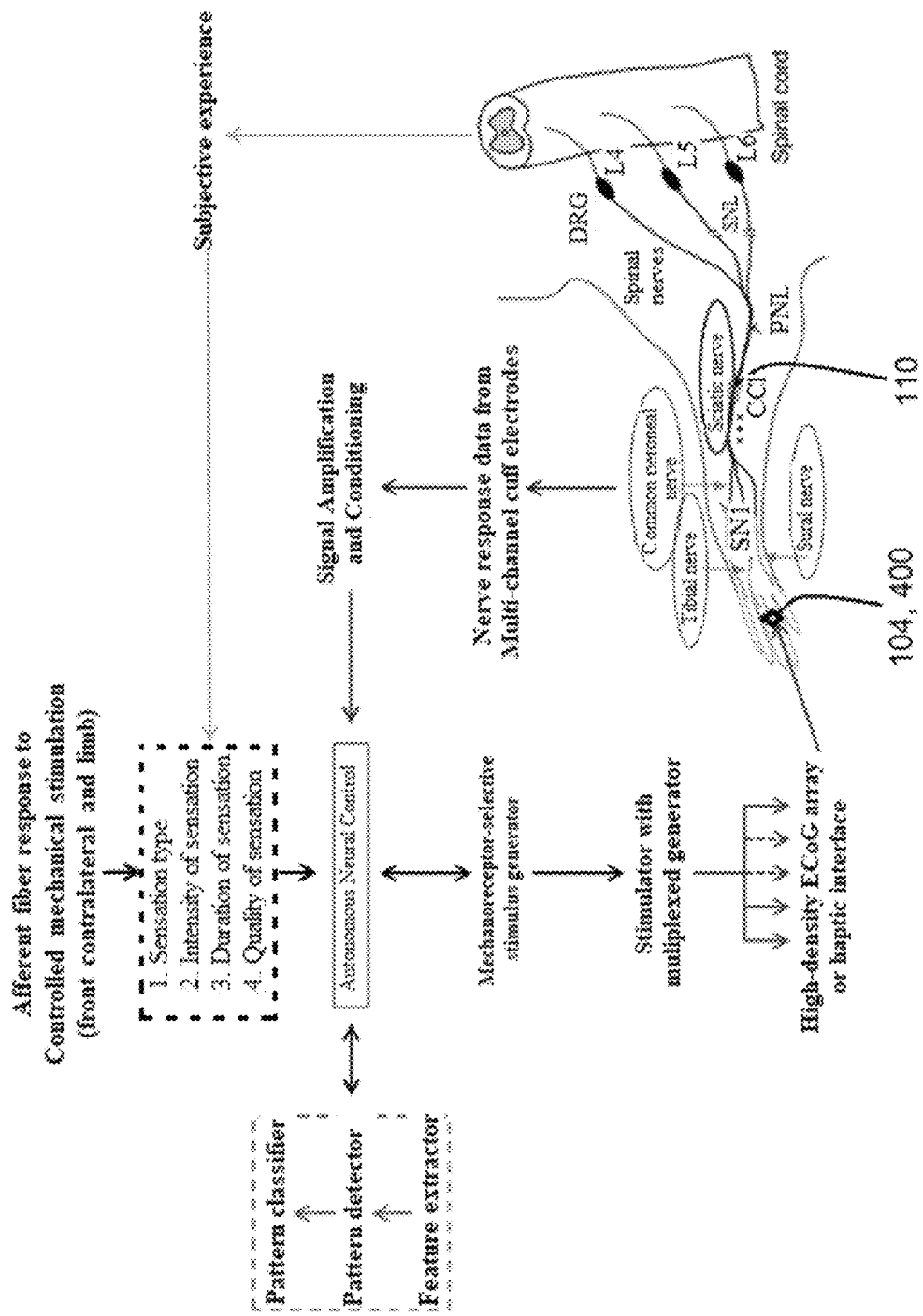
FIG. 19 shows a pathway of feedback, response data, and experience data relating to cuff electrodes applied to/within a left hind limb of a rat, according to an exemplary embodiment of the present disclosure.

The information referenced in FIG. 19 and presented above involves a receptor identification/classification approach, and sensory restoration approach. Regarding a rodent experiment (the image shown in FIG. 19 is that of the left hind limb of a rat), it was noted that subjective input can only come from human tests, and that subjective feedback can accelerate the development of the sensory restoration interface.

In the present study, and as shown in FIG. 19, multiple cuff electrodes 292 (of exemplary neural sensors 110) were used record afferent fiber activation, noting that cutaneous electrodes can be used with human users. Sural, tibial and common peroneal cuff electrodes 292 were identified to aid mechanoreceptor classification by fiber group & physical (spatial) location of the mechanoreceptor. The sciatic cuff enabled conduction and velocity-dependent identification of fiber groups represented in a train of CAP responses arising from mechanoreceptor activation. The combination of cuffs enabled the classification of a "burst" of responses from a specific fiber population vs. a single CNAP from multiple fiber groups. The combination of cuffs also enabled the classification of a "burst" of responses from a >1 fiber population linked to a specific mechanoreceptor subtype.

In human or rat experiments, multiple forms of mechanical stimulation can be presented to the contralateral hand or hind limb to mimic a "real world" sensation. In rats, nerve responses are recorded and classified with respect to the mechanical stimulus (e.g., type, texture, gradient, etc.). In humans, nerve responses are recorded and classified with respect to the mechanical stimulus and the subjective experience of the stimulus, allowing for the design of a fully-personalized sensory restoration interface as generally referenced herein, such as an interface that trains itself by associating context-dependent feedback from the user with specific, fiber-selective patterns of activation as described herein and generally shown in FIG. 1.

Methods of mechanoreceptor response identification from the measured afferent CNAP response (or response train) provide for fast versus slow adaptation (e.g., duration or type of neural response as a function of stimulus duration—mechanical or electrical), frequency-selective activation, pressure-selective activation (e.g., intensity of stimulation, which may activate superficial or deep mechanoreceptors), and spatial-selective activation (e.g., point of stimulation).

Methods of mechanoreceptor-selective stimulation to mimic a "real world" mechanical stimulus (used individually or in combination) can include an initial ultra high-frequency burst of stimuli to silence rapidly adapting mechanoreceptors followed by personalized pattern of stimuli matched to the response pattern which a pattern classifier identified and stored along with a receptor activation profile (RAP) for slowly adapting mechanoreceptors in ANC, such as selective stimulation for Ruffini corpuscles and Merkel disks with frequency-selective activation, including, but not limited to, Merkel disks (5-15 Hz), Meisner corpuscles (10-50 Hz), and Pacinian corpuscles (200-300 Hz).

Depth-selective stimulation is also provided, such as burst modulated stimuli versus conventional rectangular stimuli. This can be implemented for use to exclude or include superficial or deep mechanoreceptor subtypes, for example.

Spatial-selective stimulation, such as to choose an optimal electrode pair within a grid of electrodes to limit the spatial extent of the stimulus and to provide a higher-resolution representation of a real world sensation to the user, can also be implemented. For example, a high resolution sensation can be artificially sensed by a user using the combination of, a high-resolution grid of electrodes with defined spatial locations on the receptor field, parallel stimulation from multiple electrode pairs chosen according to the sensor locations on a prosthesis, and/or complex, patterned stimuli from each electrode pair for selective activation of individual or multiple mechanoreceptor subtypes.

Charge-duration line summary equations for an exemplary TMR6 left sciatic nerve stimulus response profile were also obtained via operation of an exemplary device 100 of the present application. For example, and for a mixed A-fiber population ($V_{Afibers,Max}=1.473155E-04$ V):

Maximal (i.e., 100%) activation threshold equation (from measured data):

$$Q_{max}=0.00035398*t_{st}+8.4072E-09, [R^2=1],$$
$$[\tau_{SD}=2.375E-05 \text{ sec}]$$

25% maximal activation threshold equation (from measured data):

$$Q_{25\%Max}=0.00017411*t_{st}+1.1401E-08, [R^2=0.98023],$$
$$[\tau_{SD}=6.5484E-05 \text{ sec}]$$

Minimal (i.e., 0%) activation threshold equation (predicted from ANC Model Equations):

$$Q_{0\%Max,Pred}=0.00011415*t_{st}+9.0627E-09,$$
$$[\tau_{SD,Pred}=7.9395E-05 \text{ sec}]$$

Rheobase-%Maximal Activation Relationship $$I_{Rh,Pred}=2.3984E-06*\%Act+1.1415E-04$$

For an exemplary C-fiber Population ($V_{Cfibers,Max}=4.245585E-04$ V):

Maximal (i.e., 100%) activation threshold equation (from measured data):

$$Q_{Max}=0.00019456*t_{st}+2.1676E-08, [R^2=0.98917],$$
$$[\tau_{SD}=0.00011141 \text{ sec}]$$

25% maximal activation threshold equation (from measured data):

$$Q_{25\%Max}=0.0001808*t_{st}+1.0393E-08, [R^2=0.99995],$$
$$[\tau_{SD}=5.7482E-05 \text{ sec}]$$

Minimal (i.e., 0%) activation threshold equation (predicted from ANC Model Equations):

$$Q_{0\%Max,Pred}=0.00017621*t_{st}+6.9614E-09,$$
$$[\tau_{SD,Pred}=3.9506E-05 \text{ sec}]$$

Rheobase-%Maximal Activation Relationship $$I_{Rh,Pred}=1.8350E-07*\%Act+1.7621E-04$$

For each of the foregoing:
1. All numbers are presented in SI units
2. %maximal activation can be estimated as a proportion of $V_{Max}$ for the fiber type of interest
3. $Q_{Max}$ and $Q_{0\%Max,Pred}$ correspond to the lines plotted in the accompanying figure
4. Q=charge/phase (in coulombs)
5. $I_{Rh}$=rheobase current and slope of charge-duration line (in amps)
6. $t_{st}$=pulse duration (in sec)
7. $\tau_{SD}$=strength-duration time constant and x-intercept (in sec)

While various embodiments of devices for sensory prosthesis devices and systems and methods for using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

The disclosure referenced herein is inclusive of combinations of the aspects described herein. References to "a particular aspect" (or "embodiment" or "version") and the like refer to features that are present in at least one aspect of the present disclosure. Separate references to "an aspect" (or "embodiment") or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A feedback system, comprising:
a prosthesis configured to be worn by an individual, the prosthesis comprising:
at least one prosthesis sensor configured to detect a state or condition in an environment of the at least one prosthesis sensor, and
at least one actuator in communication with the at least one prosthesis sensor and configured to receive data relating to the detected state or condition and to stimulate a nerve of the individual;
a neural sensor positioned upon or within the individual, the neural sensor configured to detect a neural response relating to a stimulation of the nerve by the at least one actuator; and
a processor in communication with at least one of the at least one prosthesis sensor, at least one of the at least one actuator, and the neural sensor, the processor configured to control operation of the at least one actuator based upon the data relating to the detected state or condition from the at least one prosthesis sensor and data from a sensation map.

2. The feedback system of claim 1, wherein the processor is further configured to predict one or more sensations that the individual may experience using sensation data from the sensation map relating to one or more experienced sensations from a brain of the individual in response to the neural response.

3. The feedback system of claim 1, wherein the at least one actuator is configured to directly or indirectly stimulate the nerve of the individual.

4. The feedback system of claim 1, wherein the at least one actuator is configured to vibrate in response to the state or condition when the state or condition indicates vibration.

5. The feedback system of claim 1, wherein the at least one actuator comprises an array of actuators in communication with the processor via a plurality of signal pathways.

6. The feedback system of claim 1, wherein the system further comprises the sensation map, and wherein the sensation data of the sensation map further relates to a second experienced sensation from the brain of the individual in response to a second neural response.

7. The feedback system of claim 1, wherein the system further comprises the sensation map comprising sensation data that relates to one or more experienced sensations from a brain of the individual in response to one or more neural responses.

8. The feedback system of claim 1, accessible using a data processing system in communication with the feedback system, the data processing system comprising:
a data processor in communication with the feedback system, a data storage system, and a user interface system, wherein the data storage system is configured to store data processed by the data processor from the feedback system, and wherein the user interface system is configured to obtain inputs from a user to control operation of the data processor.

9. The feedback system of claim 8, wherein the data processor is controllable by a second data processing system in communication with the data processor through a network.

10. The feedback system of claim 1, wherein the at least one actuator comprises:
a plunger positioned relative to an electromagnetic coil, the plunger having a tip configured to provide physical pressure to the nerve of the individual, the plunger configured for displacement from current flowing through the electromagnetic coil;
a spring positioned relative to the plunger, the spring configured to oppose a force related to movement of the plunger; and
a pressure sensor positioned relative to the spring, the pressure sensor configured to measure pressure provided by the plunger.

11. The feedback system of claim 10, wherein the at least one actuator further comprises at least one heating element configured to stimulate the nerve of the individual with heat, at least one cooling element configured to stimulate the nerve of the individual via cooling, or both.

12. The feedback system of claim 11, wherein the at least one actuator stimulates the nerve of the individual with heat via operation of the at least one heating element in response to the detected state or condition from the at least one prosthesis sensor and data from the sensation map relating to heat.

13. The feedback system of claim 11, wherein the at least one actuator stimulates the nerve of the individual with cooling via operation of the at least one cooling element in response to the detected state or condition from the at least one prosthesis sensor and data from the sensation map relating to cooling.

14. The feedback system of claim 10, wherein the plunger provides the physical pressure to the nerve of the individual in response to the detected state or condition from the at least one prosthesis sensor and data from the sensation map relating to pressure.

15. A method, comprising the steps of:
collecting sensor data from a sensor of a prosthesis;
applying actuation via an actuator of the prosthesis corresponding to the sensor data to induce a neural response from a nerve of an individual wearing the prosthesis;
receiving data of a sensation corresponding to a neural response from the individual; and
generating a sensation map relating the sensor data to the data of the sensation.

16. The method of claim 15, further comprising the step of:
repeating the collecting, applying, receiving, and generating steps to generate a comprehensive sensation map corresponding to the sensor, wherein the sensor data and the data of the sensation within the comprehensive sensation map is used to further apply actuation of the actuator by way of movement of a plunger of the actuator to provide physical pressure to the nerve of the individual.

17. The method of claim 15, wherein the sensor data and the data of the sensation within the sensation map is used to further apply actuation of the actuator by way of operation of at least one heating element of the actuator to the individual in response to the data of the sensation indicating heat from the sensor of the prosthesis.

18. The method of claim 15, wherein the sensor data and the data of the sensation within the sensation map is used to further apply actuation of the actuator by way of operation of at least one cooling element of the actuator to provide cooling to the individual in response to the data of the sensation indicating cooling from the sensor of the prosthesis.

19. An actuator comprising:
a plunger positioned relative to an electromagnetic coil, the plunger having a tip configured to provide physical pressure to a nerve of an individual, the plunger configured for displacement from current flowing through the electromagnetic coil;
at least one heating element configured to stimulate the nerve of the individual with heat; and
at least one cooling element configured to stimulate the nerve of the individual via cooling;
wherein operation of the actuator is controlled using a processor in communication with the actuator, the processor configured to control operation of the actuator based upon data obtained by a sensor of a prosthesis configured to be worn by the individual and a sensation map comprising sensation data relating to an experienced sensation from a brain of the individual.

20. The actuator of claim 19, wherein the actuator is configured to a) provide physical pressure based upon pressure data obtained by the sensor of the prosthesis, b) provide the heat based upon heat data obtained by the sensor of the prosthesis, and c) provide the cooling based upon cooling data obtained by the sensor of the prosthesis.

* * * * *